United States Patent [19]

Nagase et al.

[11] Patent Number: 5,144,078
[45] Date of Patent: Sep. 1, 1992

[54] FLUORINE CONTAINING DIAMINOBENZENE DERIVATIVES AND ITS USE

[75] Inventors: Yu Nagase; Yuriko Takamura, both of Sagamihara; Noriaki Kohtoh, Funabashi; Hiroyoshi Fukuro, Funabashi; Toyohiko Abe, Funabashi, all of Japan

[73] Assignees: Sagami Chemical Research Center; Nissan Chemical Industries, Ltd., both of Tokyo, Japan

[21] Appl. No.: 676,555

[22] Filed: Mar. 28, 1991

[30] Foreign Application Priority Data

Mar. 30, 1990 [JP]  Japan ................................. 2-80855

[51] Int. Cl.$^5$ .................. C07C 211/00; C08G 8/02
[52] U.S. Cl. ................................. 564/472; 528/125; 528/183; 528/336; 528/350; 528/351; 528/353
[58] Field of Search ................ 564/442; 528/353, 183, 528/350, 125, 128, 351, 336

[56] References Cited

U.S. PATENT DOCUMENTS

| | | | |
|---|---|---|---|
| 4,713,438 | 12/1987 | Harris et al. | 528/337 |
| 4,731,450 | 3/1988 | Wakselman et al. | 546/303 |
| 5,075,392 | 12/1991 | Harris et al. | 525/420 |

*Primary Examiner*—John Kight, III.
*Assistant Examiner*—Shelley A. Wright
*Attorney, Agent, or Firm*—Oliff & Berridge

[57] ABSTRACT

The present invention relates to a novel fluorine-containing diaminobenzene derivatives having a perfluoroalkyl group and to a novel fluorine-containing polyimide which is produced from the said diaminobenzene as a starting material and to a novel polyimide having both a fluorine-containing group and/or a siloxane chain in the side chain thereof, the polyimide being produced from the said fluorine-containing diaminobenzene and fluorine-containing polyimide and to a liquid crystal-aligning agent with an elevated tilt angle, which contains a polyimide having a fluorine-containing group and a siloxane chain.

1 Claim, No Drawings

FLUORINE CONTAINING DIAMINOBENZENE DERIVATIVES AND ITS USE

FIELD OF THE INVENTION

The present invention relates to a novel fluorine-containing diaminobenzene derivative having a perfluoroalkyl group and to a novel fluorine-containing polyimide and a novel polyimide having both a fluorine-containing group and a siloxane chain in the side chain thereof, both of which are produced from a starting material of the said diaminobenzene derivative and have excellent heat-resistance and solvent-resistance and also an excellent surface characteristc. It also relates to a liquid crystal-aligning agent, which contains a polyimide having a fluorine-containing group and/or a siloxane chain in the side chain thereof, the polyimide being produced from a starting material of a fluorine-containing diaminobenzene derivative having a perfluoroalkyl group and/or a siloxane-containing diaminobenzene derivative having a siloxane chain and having excellent heat-resistance and solvent-resistance and also an excellent surface characteristic. Where a substrate for a liquid crystal is treated with the liquid crystal-treating agent, liquid crystal molecules as provided on the substrate may well be aligned to the substrate with an elevated tilt angle. In particular, the polyimide of the present invention, which has both a fluorine-containing group and a siloxane chain in the side chain thereof, may be formed into a film which displays excellent heat-resistance, permeability and separatability when used in separation of a gaseous mixture or a liquid mixture. It may well be thinned with ease to give a thin film having a sufficient film strength and a high separating capacity. The film is therefore useful as a separation film.

BACKGROUND OF THE INVENTION

Hitherto, aromatic polyimides have widely been used as protecting materials, insulating materials and adhesives in the filed of electronic appliances and also as films or construction materials in other various fields, because of their high mechanical strength, heat-resistance and solvent-resistance. However, conventional polyimides have various drawbacks that the shaping workability is poor, the flexibility is poor, the wet stability is poor and the adhesiveness to inorganic materials such as silicone wafer or glass is insufficient. In order to overcome the drawbacks, modified polyimides having various chemical structures have been produced and studied in these days. Above all, a technique of producing a polyimide/polysiloxane block copolymer from a polyimide precursor to be obtained by substituting a part of the diamine component of a starting material of a polyimide by a polysiloxane having a diamino group at the both terminals thereof has been proposed, for the purpose of improving the flexibility and adhesiveness to inorganic materials among the necessary properties of polyimides. (For instance, refer to JP-A-57-143328, 58-7473, 58-13631, 61-83228 and 61-118424. The term "JP-A" as used herein means an "unexamined published Japanese patent application".) However, such block copolymers may have improved flexibility and adhesiveness but, on the other hand, have a problem that the filming capacity is lowered with increase of the siloxane content in the copolymer.

There is another proposal of using an aromatic polyimide as a gas-separating film material. (Refer to JP-A-57-15819.) As the film of the kind made of such an aromatic polyimide has an excellent selective permeability especially to hydrogen gas, it has already been put to practical use. Since the gas permeability coefficient of such an aromatic polymide film is generally small, the film may well be applied to a gas having a relatively small molecular size and having a high diffusibility through the film, such as hydrogen gas. However, the film is unsuitable to separation of any other gas, such as oxygen or carbon dioxide because of such a small gas permeability coefficient. Additionally, there are few examples of using a polyimide film as a liquid-separating film. As one example, there is a report relating to separation of a water/ethanol mixture with a polyamic acid film which has been controlled with respect to its imidation percentage (refer to *Polymer Preprints, Japan*, Vol. 36, 1987, page 2021). However, also in the case, as the permeability coefficient of the reported film is relatively small, the film could not be said to be practically usable.

In order to elevate the gas and liquid permeability of a polyimide film, copolymerization with a material having a high substance permeability like the above-mentioned polyimide/polysiloxane copolymer could be proposed. In fact, however, there is no report relating to gas or liquid separation with such a copolymer up to this date because of the problem on the filming property of the copolymer. On the other hand, the present inventors previously investigated various matters for the purpose of obtaining new film materials of aromatic polyimides which have excellent mechanical strength, heat-resistance and solvent-resistance of aromatic polyimides of themselves and have sufficient liquid permeability and separatability of a practical level. As a result, they have found that production of a polysiloxane macromonomer having a diaminophenyl group at one terminal thereof and having an organosiloxane repeating unit is possible, that polycondensation of the macromonomer gives a siloxane-containing polyimide via a siloxane-containing polyimide precursor, and that the film to be obtained from the resulting siloxane-containing polyimide has excellent mechanical strength, heat-resistance, solvent-resistance and flexibility and also has an excellent gas or liquid selective permeability (refer to JP-A-1-204931).

On the other hand, in the field of a liquid crystal-aligning agent, an organic resin film such as a polyimide resin film or the like has heretofore been used most popularly as a substrate-treating agent, which is applied to a transparent substrate such as a transparent glass or plastic film as combined with a transparent electrode so as to orient nematic liquid crystal molecules almost in parallel to the treated substrate.

In the case, it is known that the organic resin film as formed on the substrate is rubbed with a cloth in a determined direction, whereby the liquid crystal molecules as provided on the substrate are oriented to the rubbed direction to simultaneously yield a liquid crystal tilt angle of generally from 1 to 3 degrees to the surface of the substrate.

As a method of greatly tilting and orienting liquid crystal molecules to the substrate, a method of depositing an inorganic film such as a silicon oxide film on a substrate by vapor deposition has heretofore been known.

The present inventors earnestly investigated various polyimides so as to further improve the poor wet stability of polyimides of themselves as well as the surface characteristic and separation characteristic of siloxane-containing polyimide films by introducing a fluorine-containing group into the side chain of general polyimides or the above-mentioned siloxane-containing polyimides to thereby elevate the water-repelling property of the surface of the film to be obtained from the resulting polyimide. As a result, they have found a technique of producing a novel fluorine-containing diaminobenzene derivative having a perfluoroalkyl group, and a technique of producing a novel fluorine-containing polyimide and a novel polyimide having both a fluorine-containing group and a siloxane chain in the side chain thereof by polycondensation of the said novel derivative followed by imidation of the resulting polycondensate, and they have further found that the polyimides thus obtained have a high water-repelling property because of the characteristic of the fluorine-containing group therein.

In the filed of a liquid crystal-aligning agent, a method of rubbing an organic resin film as formed on a substrate has heretofore been carried out. In the method, however, it is difficult to sufficiently largely tilt and orient the liquid crystal molecules as provided on the rubbed film.

On the other hand, a method of depositing an inorganic film on a substrate by vapor deposition is more complicated than the rubbing method and therefore it is not always a suitable method in practical industrial production of liquid crystal devices.

Under the situation, it has been found that a satisfactory liquid crystal-aligning agent for liquid crystal cells can be produced from the polyimides of the present invention. Precisely, the liquid crystal-aligning agent containing the novel polyimide of the present invention yields a sufficiently large tilt angle when applied to a substrate of liquid crystal cell. On the basis of the findings, the present inventors have achieved the present invention.

JP-A-62-142099 has proposed a liquid crystal-aligning agent, which comprises a reaction product of a long-chain alkylamine and a polyimide resin precursor. JP-A-64-25126 has proposed a liquid crystal-aligning agent, which comprises a polyimide as derived from a starting material of an alkyl group-having diamine.

However, it is unknown that a liquid crystal-aligning agent, which comprises a polyimide having a fluorine-containing group and/or a siloxane chain in the side chain thereof, the polyimide being obtained from a starting material of a fluorine-containing diaminobenzene derivative and/or a siloxane-containing diaminobenzene derivative, like the present invention, yields an extremely large tilt angle of liquid crystal molecules.

SUMMARY OF THE INVENTION

The first object of the Present invention is to provide a novel fluorine-containing diaminobenzene derivative having a perfluoroalkyl group.

The second object of the present invention is to provide a novel fluorine-containing polyimide which is produced from the said diaminobenzene as a starting material.

The third object of the present invention is to provide a novel polyimide having both a fluorine-containing group and/or a siloxane chain in the side chain thereof, the polyimide being produced from the said fluorine-containing diaminobenzene and fluorine-containing polyimide.

The fourth object of the present invention is to provide a liquid crystal-aligning agent with an elevated tilt angle, which contains a polyimide having a fluorine-containing group and a siloxane chain.

DETAILED EXPLANATION OF THE INVENTION

The present invention relates to (1) a fluorine-containing diaminobenzene derivative of a general formula (I):

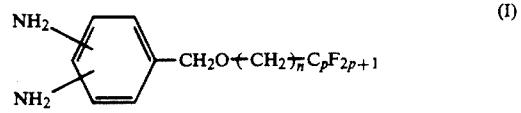

where n represents an integer of from 1 to 6, and p represents an integer of from 1 to 12;

(2) a polyimide which is produced from a starting compound of the said derivative and which comprises repeating units of general formulae (II) and (III):

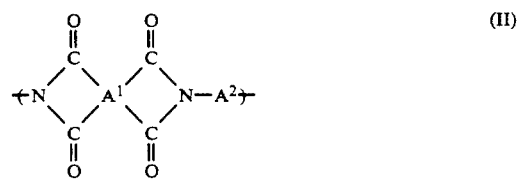

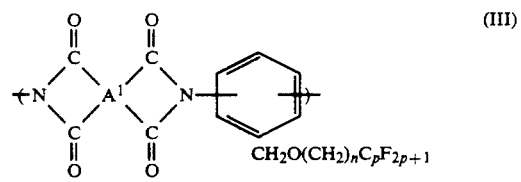

where $A^1$ represents a tetravalent carbon-cyclic aromatic group, $A^2$ represents a divalent organic group having an aromatic group, n represents an integer of from 1 to 6, and p represents an integer of from 1 to 12, provided that n, p, $A^1$ and $A^2$ may optionally be different ones in every repeating unit, in which the molar ratio of the repeating unit of the formula (III) falls within the range of from 1 to 100%, the polyimide having a weight average molecular weight of 10,000 or more and having a fluorine-containing group in the side chain; and (3) a polyimide comprising repeating units of general formulae (II), (III) and (IV):

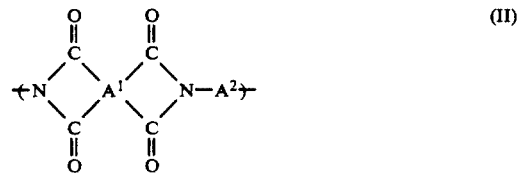

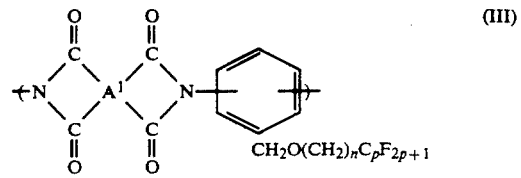

(IV)

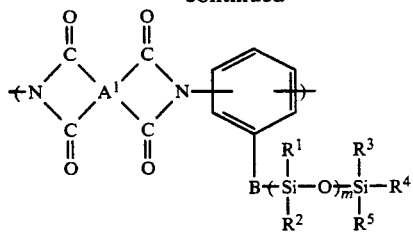

where $A^1$ represents a tetravalent carbon-cyclic aromatic group, $A^2$ represents a divalent organic group having an aromatic group, B represents a divalent organic group, $R^1$ to $R^5$ may be same or different and each represents an alkyl group, a substituted alkyl group, a phenyl group or a substituted phenyl group, m represents an integer of 1 or more, n represents an integer of from 1 to 6, and p represents an integer of from 1 to 12, provided that n, p, m, $A^1$, $A^2$, B, $R^1$ and $R^2$ may optionally be different ones in every repeating unit, in which the molar ratio of the repeating unit of the formula (II) falls within the range of from 0 to 98%, that of the repeating unit of the formula (III) within the range of from 1 to 99% and that of the repeating unit of the formula (IV) within the range of from 1 to 99, the polyimide having a weight average molecular weight of 10,000 or more and having a fluorine-containing group and a siloxane group in the side chain.

The present invention further relates to a liquid crystal-aligning agent which contains a polyimide comprising repeating units of general formulae (V), (VI) and (VII):

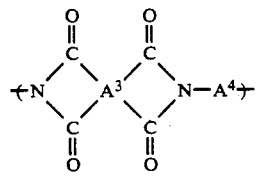 (V)

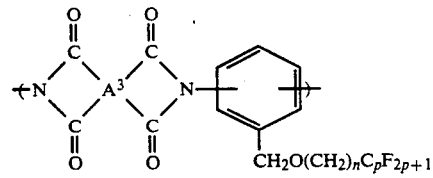 (VI)

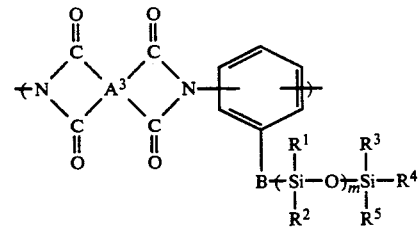 (VII)

where $A^3$ represents a tetravalent organic group of constituting a tetracarboxylic acid, $A^4$ represents a divalent organic group of constituting a diamine, B represents a divalent organic group, $R^1$ to $R^5$ may be same or different and each represents an alkyl group, a substituted alkyl group, a phenyl group or a substituted phenyl group, m represents an integer of 1 or more, n represents an integer of from 1 to 6, and p represents an integer of from 1 to 12, provided that n, p, m, $A^3$, $A^4$, B, $R^1$ and $R^2$ may optionally be different ones in every repeating unit, and the repeating units satisfy the condition of:

$$a+b+c=1$$

$$0 \leq a < 1$$

$$0 \leq b \leq 1$$

$$0 \leq c \leq 1,$$

where a means a molar ratio of the repeating unit of the formula (V), b means a molar ratio of the repeating unit of the formula (VI), and c means a molar ratio of the repeating unit of formula (VII), the polyimide having a weight average molecular weight of 10,000 or more and having a fluorine-containing group and/or a siloxane group in the side chain thereof.

As examples of the tetravalent carbon-cyclic aromatic group of $A^1$ in the above-mentioned formulae (II), (III) and (IV), the following structural formulae are referred to.

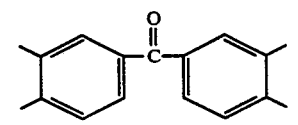
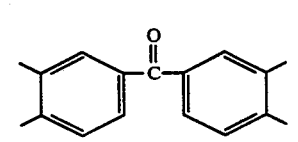
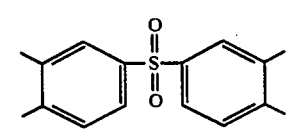
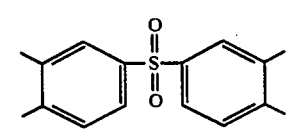

-continued

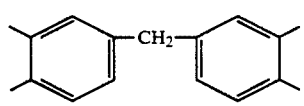,

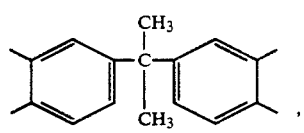,

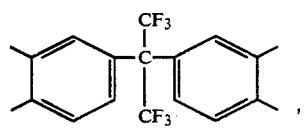,

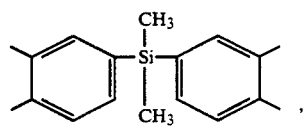,

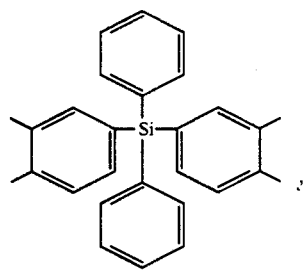,

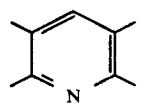,

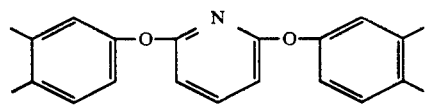

The tetravalent organic group of constituting a tetracarboxylic acid, which is represented by $A^3$ in formulae (V), (VI) and (VII), may be same as or different from the above-mentioned tetravalent carbon-cyclic aromatic group of $A^1$. Additionally, the group $A^3$ may further include a tetravalent alicyclic group, for example, those of the following formulae:

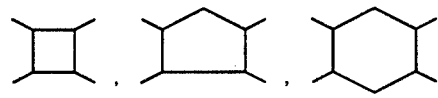

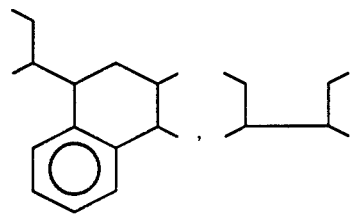

as well as a tetravalent aliphatic group.

As examples of the divalent organic group containing an aromatic group, which is represented by $A^2$ in the above-mentioned formula (II), the following structural formulae are referred to.

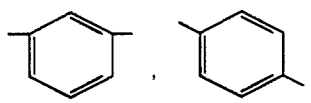

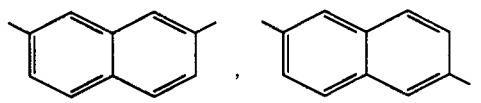,

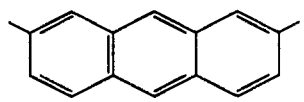,

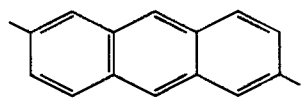,

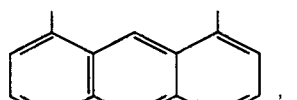,

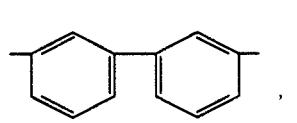,

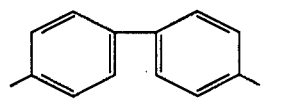,

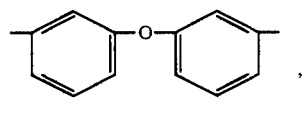,

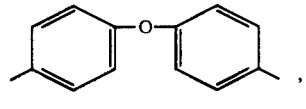,

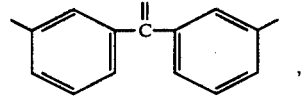,

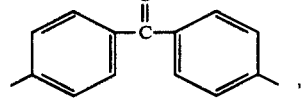,

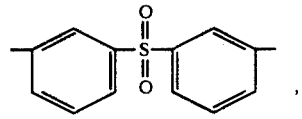,

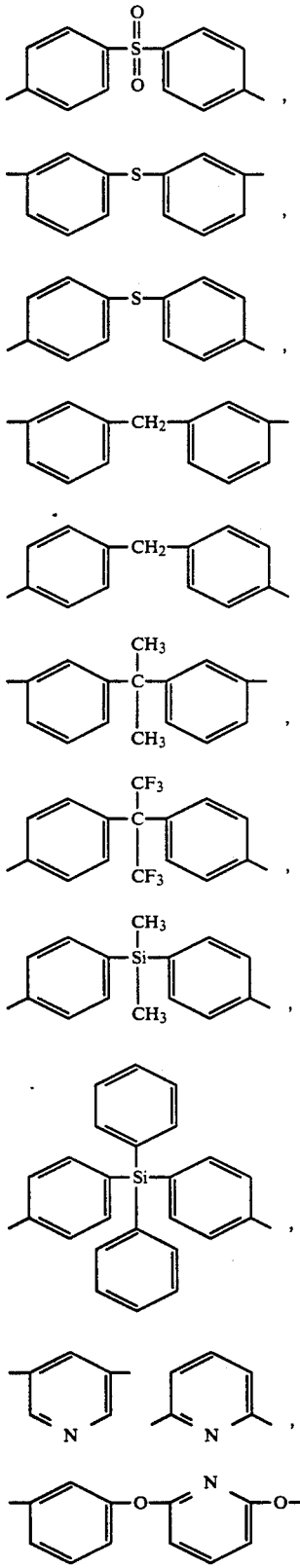

organic group of $A^2$, and it may further include an alicyclic or aliphatic divalent organic group.

As examples of the divalent organic group of B in the above-mentioned formulae (IV) and (VII), there are mentioned a substituted or unsubstituted methylene group as well as a polymethylene group, a silylene-polymethylene group, a phenylene-polymethylene group, an oxy-polymethylene group and a phenyleneoxy-polymethylene group each having 2 or more carbon atoms.

Fluorine-containing diaminobenzene derivatives of the above-mentioned formula (I) of the present invention can be prepared, for example, by the method mentioned below.

Precisely, a dinitrobenzyl halide of a general formula (VIII):

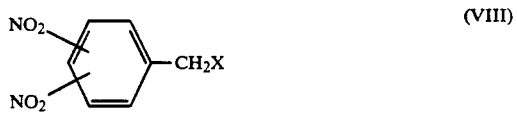

(VIII)

where X represents a halogen atom, is first reacted with a fluorine-containing alcohol of a general formula (VIV):

(VIV)

where n represents an integer of from 1 to 6, and p represents an integer of from 1 to 12, in a solvent in the presence of a base to form a dinitrobenzene derivative of a general formula (X):

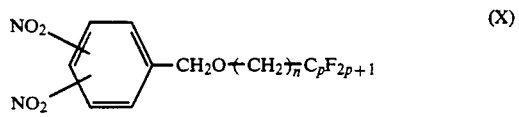

(X)

where n represents an integer of from 1 to 6, and p represents an integer of from 1 to 12; and thereafter the dinitro group in the compound of formula (X) is reduced by an ordinary method to a diamino group to finally produce the intended diaminobenzene derivative of the above-mentioned formula (I).

As examples of dinitrobenzyl halides of the above-mentioned formula (VIII), there are mentioned 3,5-dinitrobenzyl chloride, 3,5-dinitrobenzyl bromide, 3,5-dinitrobenzyl iodide, 2,4-dinitrobenzyl chloride, 2,4-dinitrobenzyl bromide, 2,4-dinitrobenzyl iodide, 2,5-dinitrobenzyl chloride, 2,5-dinitrobenzyl bromide, 2,3-dinitrobenzyl chloride and 2,3-dinitrobenzyl bromide. As examples of fluorine-containing alcohols of the above-mentioned formula (IX), there are mentioned 2,2,2-trifluoroethanol, 2,2,3,3,3-pentafluoro-1-propanol, 3,3,3-trifluoro-1-propanol, 1H,1H,2H,2H-pentafluoro-1-butanol, 3,3,3-trifluoro-1-butanol, 1H,1H-nonafluoro-1-pentanol, 1H,1H,2H,2H-heptafluoro-1-pentanol, 3,3,3-trifluoro-1-pentanol, 1H,1H-undecafluoro-1-hexanol, 1H,1H,2H,2H-nonafluoro-1-hexanol, 3,3,3-trifluoro-1-hexanol, 3,3,3-trifluoro-1-heptanol, 1H,1H-pentadecafluoro-1-octanol, 1H,1H,2H,2H-tridecafluoro-1-octanol, 1H,1H-nonadecafluoro-1-decanol, 1H,1H,2H,2H-heptadecafluoro-1-decanol, 1H,1H-trieicosafluoro-1-dodecanol, 1H,1H,2H,2H-heneicosafluoro-1-dodecanol, 1H,1H-pentaeicosafluoro-1-tridecanol and 1H,1H,2H,2H-pentaeicosafluoro-1-tetradecanol.

The divalent organic group of constituting a diamine, which is represented by $A^4$ in the above-mentioned formula (V), may be same as or different from the above-mentioned aromatic group-containing divalent As the base to be used in the reaction of the dinitrobenzyl halide of the above-mentioned formula (VIII) and the fluorine-containing alcohol of the above-mentioned formula (IX), for example, preferred are inorganic bases such as sodium hydroxide, potassium hydroxide, calcium hydroxide, sodium carbonate, potassium carbonate and sodium hydroxide. To the reaction may be applied an interphase-transferring catalyst such as tetrabutylammonium hydrogensulfate, tetrabutylammonium bromide or tetrabutylammonium iodide, so as to more smoothly carry out the reaction. The reaction preferably proceeds at a temperature near room temperature, and the solvent to be used in the reaction is preferably an organic solvent such as tetrahydrofuran, hexane, cyclohexane, benzene or toluene.

The reduction reaction of converting the dinitro compound of the above-mentioned formula (X) to the diamino compound of the present invention of the above-mentioned formula (I) may easily be effected by reducing the former with an ordinary reducing agent such as diboran, lithium borohydride, sodium borohydride, lithium aluminium hydride, sodium aluminium hydride, sodium dialkoxyaluminium hydride or sodium diethylaluminium hydride. As another means, the former dinitro compound may be reacted with a hydrosilane compound such as trichlorosilane, tripropylsilane or triethylsilane in the presence of zinc chloride to also produce the intended product. As still another means, the intermediate of formula (X) may be subjected to catalytic reduction with a metal catalyst such as nickel, platinum, palladium or rhodium to produce the final compound of furmula (I). Any of these methods is desired to be effected in a solvent, which may be anyone not participating in the reaction of itself. As examples of usable solvents, there are mentioned alcohol, tetrahydrofuran, dimethoxyethane, dioxane, benzene and toluene. The reaction temperature may fall within the range of from −100° C. to 50° C., preferably from −80° C. to 30° C.

The fluorine-containing diaminobenzene derivative of the above-mentioned formula (I), which is obtained by the above-mentioned method, may be reacted with a bifunctional compound having a reactivity with a diaminophenyl group, such as aromatic dicarboxylic acids, aromatic dicarboxylic acid dichlorides or aromatic tetracarboxylic acid dianhydrides, by polycondensation reaction to give a novel copolymer having a fluorine-containing group in the side chain thereof and having a main chain skeleton of an aromatic polyamide, polyamic acid or polyimide. The polycondensation reaction may be carried out in the presence of any other tertiary diamine compound as a tertiary component to give a copolymer having two or more kinds of diamine components. Since the graft two or more kinds of diamine components. Since the graft copolymer of the type has a main chain skeleton of a high polymer component having a heat-resistance and it also has a water-repelling property which is characteristic to the fluorine-containing group in the side chain thereof, it has a possibility of being a heat-resistant high polymer material having an excellent surface characteristic. Where the compound of formula (I) of the present invention is used as a raw material of producing such high polymer compounds, it is necessary that the number of carbon atoms in the fluorine-containing group in the fluorine-containing diaminobenzene derivative of the above-mentioned formula (I) falls within the range of from 1 to 12, more preferably from 4 to 12, in order to more effectively elevate the water-repelling property of the high polymer compounds to be obtained.

Polyimides of the present invention of the present invention, which have a fluorine-containing group in the side chain thereof and which have repeating untis of the above-mentioned formulae (II) and (III), (hereinafter referred to as "fluorine-containing polyimides") can be produced from a starting material of the diaminobenzene derivative of the above-mentioned formula (I), in accordance with the reaction process of condensation followed by imidation, which will be mentioned below.

Precisely, a tetracarboxylic acid dianhydride of a general formula (XI):

where $A^1$ represents a tetravalent carbon-cyclic aromatic group, and a fluorine-containing diaminobenzene derivative of formula (I) are fed into a reactor each in an equimolar amount, or alternatively, a tetracarboxylic acid dianhydride of the above-mentioned formula (XI) and a diamine component of a mixture comprising a fluorine-containing diaminobenzene derivative of the above-mentioned formula (I) and an aromatic diamine compound of a general formula (XII):

where $A^2$ represents a divalent organic group having an aromatic group, are fed into a reactor each in an almost equimolar amount, and the reactants are then subjected to polycondensation by an ordinary method in an organic polar solvent to give a polyamide acid. The resulting polyamide acid which is an intermediate is thereafter dehydrated under heat at a temperature of 100° to 400° C. or is subjected to chemical imidation with an ordinary imidating agent such as triethylamine/acetic anhydride, to finally produce the intended fluorine-containing polyimide having repeating units of the above-mentioned formulae (II) and (III).

Examples of tetracarboxylic acid dianhydrides of the above-mentioned formula (XI) for use in the present invention include pyromellitic acid dianhydride, 2,3,6,7-naphthalene-tetracarboxylic acid dianhydride, 1,2,5,6-naphthalene-tetracarboxylic acid dianhydride, 1,4,5,8-naphthalene-tetracarboxylic acid dianhydride, 2,3,6,7-anthracene-tetracarboxylic acid dianhydride, 1,2,5,6-anthracene-tetracarboxylic acid dianhydride, 3,3',4,4'-diphenyltetracarboxylic acid dianhydride, bis(3,4-dicarboxyphenyl)ether dianhydride, 3,3',4,4'-benzophenonetetracarboxylic acid dianhydride, bis(3,4-dicarboxyphenyl)sulfone dianhydride, bis(3,4-dicarboxyphenyl)methane dianhydride, 2,2-bis(3,4-dicarboxyphenyl)propane dianhydride, 1,1,1,3,3,3-hexafluoro-2,2-bis(3,4-dicarboxyphenyl)propane dianhydride, bis(3,4-dicarboxyphenyl)dimethylsilane dianhydride, bis(3,4-dicarboxyphenyl)diphenylsilane dianhydride, 2,3,5,6-pyridine-tetracarboxylic acid dianhydride, and 2,6-bis(3,4-dicarboxyphenoxy)pyridine dianhydride. A mixture comprising two or more of the said dianhydrides may also be employed in the present invention.

Examples of aromatic diamine compounds of the above-mentioned formula (XII) for use in the present invention include m-diaminobenzene, p-diaminobenzene, 2,7-diaminonaphthalene, 2,6-diaminonaphthalene, 2,7-diaminoanthracene, 2,6-diaminoanthracene, 1,8-diaminoanthracene, 3,3'-diaminobiphenyl, 4,4'-diaminobiphenyl, 3,3'-diaminodiphenyl ether, 4,4'-diaminodiphenyl ether, 3,3'-diaminobenzophenone, 4,4'-diaminobenzophenone, 3,3'-diaminodiphenylsulfone, 4,4'-diaminodiphenylsulfone, 3,3'-diaminodiphenylsulfone, 4,4'-diaminodiphenylsulfide, 3,3'-diaminodiphenylmethane, 4,4'-diaminodiphenylmethane, 2,2-bis(3-aminophenyl)propane, 1,1,1,3,3,3-hexafluroro-2,2-bis(4-aminophenyl)propane, bis(4-aminophenyl)dimethylsilane, bis(4-aminophenyl)diphenylsilane, 3,5-diaminopyridine, 2,6-diaminopyridine, and, 2,6-bis(3-aminophenoxy)pyridine. A mixture comprising two ro more of the said diamine compounds may also be employed in the present invention.

The fluorine-containing polyimides of the present invention, having repeating units of the above-mentioned formulae (II) and (III), are characterized by having the repeating unit of the above-mentioned formula (III). Accordingly, they may be either homopolymer of having only the repeating unit of formula (III) or copolymer of having both the repeating unit of formula (III) and the additional repeating unit of formula (II). Anyway, the molar ratio of the repeating unit of the above-mentioned formula (III) must be within the range of from 1 to 100% in the fluorine-containing polyimides of the present invention. However, in order that the fluorine-containing polyimides of the present invention may have a satisfactory water-repelling property, it is more desired that the molar ratio of the repeating unit of formula (III) in the polyimides is within the range of from 30 to 100%. In order that the fluorine-containing polyimides of the present invention may have a sufficient capability of forming thin films and that the films to be formed from the polyimides may have a sufficient strength, it is necessary that the polyimides have a weight average molecular weight (as obtained, for example, by gel permeation chromatography) of being 10,000 or more.

Other polyimides of the present invention, which have both a fluorine-containing group and a siloxane chain and have repeating units of the above-mentioned formulae (II), (III) and (IV), are produced from starting materials of a fluorine-containing diaminobenzene derivative of the above-mentioned formula (I), a tetracarboxylic acid dianhydride of the above-mentioned formula (XI), an aromatic diamine compound of the above-mentioned formula (XII) and a polyorganosiloxane having a diaminophenyl group at one terminal thereof and represented by a general formula (XIII):

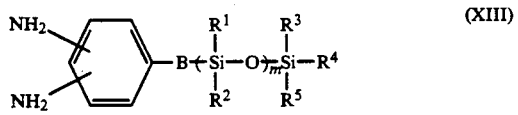

where B represents a divalent organic group, $R^1$ to $R^5$ may be same or different and each represents an alkyl group, a substituted alkyl group, a phenyl group or a substituted phenyl group, and m represents an integer of 1 or more, provided that $R^1$ and $R^2$ may be different ones in every repeating unit, in accordance with the same condensation followed by imidation as mentioned above. As the case may be, the aromatic diamine compound of the above-mentioned formula (XII) may not be added to the reaction.

Polyorganosiloxanes of the above-mentioned formula (XIII), which have a diaminophenyl group at one terminal thereof, may be produced, for example, as follows:

Precisely, a hydrogen-monoterminated polyorganosiloxane of a general formula (XIV):

where $R^1$ to $R^5$ may be same or different and each represents an alkyl group, a substituted alkyl group, a phenyl group or a substituted phenyl group, and m represents an integer of 1 or more, provided that $R^1$ and $R^2$ may be different ones in every repeating unit, is reacted with a dinitro compound of a general formula (XV):

where Y represents a group having a carbon-carbon double bond, by hydrosilylation in the presence of a catalyst to give an intermediate of a polyorganosiloxane having a dinitrophenyl group at one terminal thereof and represented by a general formula (XVI):

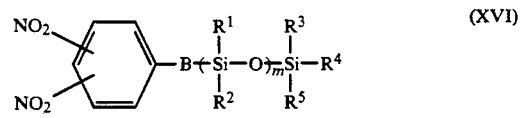

where B represents a divalent organic group, $R^1$ to $R^5$ may be same or different and each represents an alkyl group, a substituted alkyl group, a phenyl group or a substituted phenyl group, and m represents an integer of 1 or more, provided that $R^1$ and $R^2$ may be different ones in every repeating unit; and thereafter the dinitro group of the resulting intermediate compound is reduced by an ordinary method to a diamino group to thereby obtain the intended polyorganosiloxane of the above-mentioned formula (XIII).

Some of hydrogen-monoterminated polyorganosiloxanes of the above-mentioned formula (XIV) where the polymerization degree m is 1 are commercially sold. (For example, Pentamethyldisiloxane as produced by Shin-etsu Chemical Industrial Co. is referred to.) Others of formula (XIV) where m is 2 or more may be produced, for example, in accordance with the reaction process mentioned below. Briefly, an equimolar amount of an alkyl lithium compound (RLi) is added to a tri-substituted silanol to give a silanolate anion, and using the resulting anion as an initiator, a cyclosiloxane compound is polymerized by living ring-opening polymerization, whereupon the reaction is terminated with a diorganohalogenosilane compound having one Si-H bond to give the intended compound of formula (XIV). In the case, by varying the proportion of the tri-substituted silanol to the cyclosiloxane compound to be fed into the reactor, the mean polymerization degree (m) of polyorganosiloxanes of the above-mentioned formulae (XIII), (XIV) and (XVI) may be controlled. (Referential Examples 2 to 4 mentioned hereinafter are referred to.)

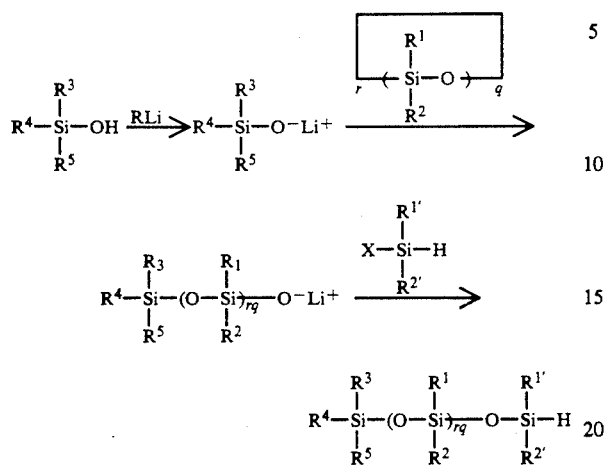

In these formulae, $R^1$ to $R^5$, $R^{1'}$ and $R^{2'}$ may be same or different and each represents an alkyl group, a substituted alkyl group, a phenyl group or a substituted phenyl group, R represents an alkyl group or a phenyl group, X represents a halogen atom, provided that $R^1$ and $R^2$ may be different ones in every repeating unit, q represents an integer of from 3 to 6, r represents an integer of 1 or more, and (rq+1) is equal to m in the above-mentioned formulae (IV), (XIV) and (XVI).

Examples of alkyl lithium compounds to be used in the reaction (RLi in the above-mentioned reaction formula) include methyl lithium, ethyl lithium, n-butyl lithium, secbutyl lithium, t-butyl lithium, n-hexyl lithium and phenyl lithium.

As examples of tri-substituted silanols of a general formula (XVII):

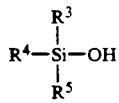
(XVII)

where $R^3$ to $R^5$ may be same or different and each represents an alkyl group, a substituted alkyl group, a phenyl group or a substituted phenyl group, which are used for production of the above-mentioned hydrogen-monoterminated polyorganosiloxanes, there are mentioned trimethylsilanol, triethylsilanol, dimethyloctylsilanol, dimethyloctadecylsilanol, 3-chloropropylmethylsilanol, 3,3,3-trifluoropropyldimethylsilanol, tridecafluoro-1,1,2,2-tetrahydrooctyldimethylsilanol, diphenylmethylsilanol, triphenylsilanol and pentfluorophenyldimethylsilanol. Some of these silanol compounds are commercially sold. Anyway, these silanol compounds may easily be produced from the corresponding chlorosilanes. As examples of cyclosiloxane compounds of a general formula (XVIII):

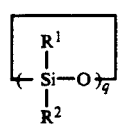
(XVIII)

where $R^1$ and $R^2$ may be same or different and each represents an alkyl group, a substituted alkyl group, a phenyl group or a substituted phenyl group, and q represents an integer of from 3 to 6, the following compounds are referred to.

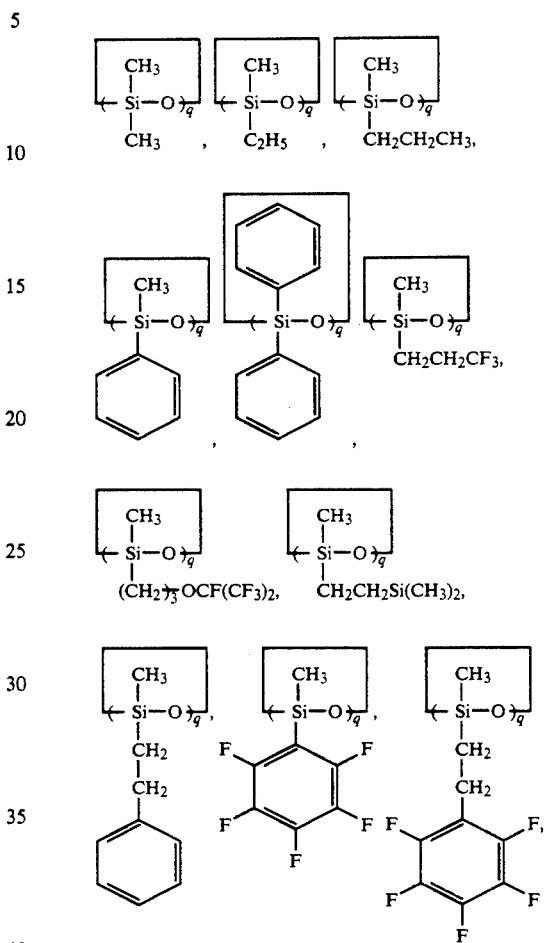

A mixture comprising two or more of these cyclosiloxane compounds may also be used in the present invention. As examples of diorganohalogenosilane compounds of a general formula (XIX):

(XIX)

where $R^{1'}$ and $R^{2'}$ may be same or different and each represents an alkyl group, a substituted alkyl group, a phenyl group or a substituted phenyl group, and X represents a halogen atom, which are used as a stopper in the above-mentioned reaction, there are mentioned dimethylchlorosilane, diethylchlorosilane, methyloctylchlorosilane, 3,3,3-trifluoropropylmethylchlorosilane, phenylmethylchlorosilane, diphenylchlorosilane, and pentafluorophenylmethylchlorosilane.

The reaction of producing hydrogen-monoterminated polyorganosiloxanes of the above-mentioned formula (XIV) in accordance with the procedure mentioned above is preferably effected in a solvent. As examples of usable solvents, organic solvents such as tetrahydrofuran, diethylether, hexane, cyclohexane and benzene are mentioned. The reaction is generally effected at a temperature near room temperature desirably in an inert atmosphere such as argon or nitrogen.

It is indispensable that the dinitro compound of the above-mentioned formula (XV), which is used in production of the polyorganosiloxane of the above-mentioned formula (XVI) having a dinitrophenyl group at one terminal thereof from the hydrogen-monoterminated polyorganosiloxane of the above-mentioned formula (XIV), has a carbon-carbon double bond. As examples of the dinitro compound, the following compounds are referred to, where the nitro groups are bonded to any two carbon atoms of 2-positioned to 6-positioned carbons of the benzene ring.

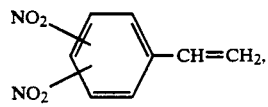

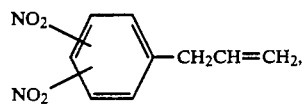

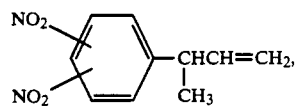

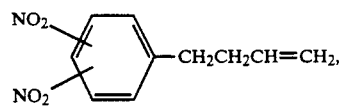

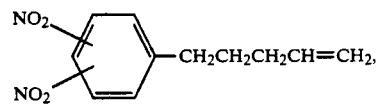

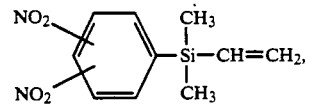

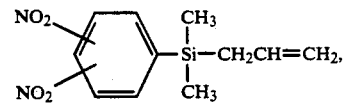

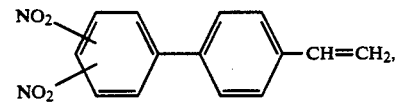

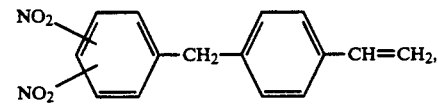

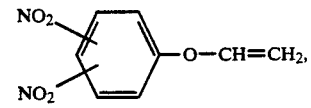

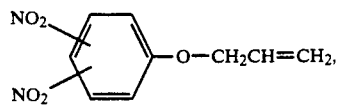

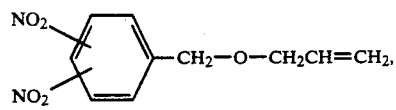

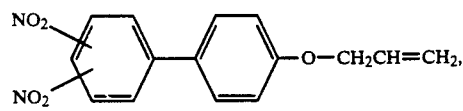

Though not available as commercial products, these compounds can easily be produced, for example, by the method of Referential Example 1 which will be mentioned hereinafter.

As the catalyst to be used for hydrosilylation of the dinitro compound of the above-mentioned formula (XV) with the hydrogen-monoterminated polyorganosiloxane of the above-mentioned formula (XIV), a platinum catalyst such as platinum metal, chloroplatinic acid or dicyclopentadienyl platinum dichloride is most popularly used. In addition, any other metal complexes such as palladium or rhodium complexes may also be used as the catalyst. For instance, usable catalysts include $(Ph_3P)_4Pd$, $(Ph_3)_2PdCl_2$, $(PhCN)_2PdCl_2$, $(Ph_3P)_3RhCl$, $(Ph_2PH)_2RhCl$, $(Ph_3P)_2(CO)PhCl$, and $[(C_2H_5)_3P]_2(CO)PhCl$. In general, the amount of the catalyst to be used for the reaction may well be approximately from 1/100 to 1/1000 equivalent to the carbon-carbon double bond-having group. The reaction is desirably effected in a solvent. As the solvent usable for the reaction, there are mentioned, for example, hexane, benzene, toluene, acetone, trichloroethylene, carbon tetrachloride and tetrahydrofuran (THF). The reaction temperature is generally within the range of from 40° C. to 100° C., and the reaction is preferably effected in an inert gas atmosphere such as argon or nitrogen.

The reduction reaction for producing the plyorganosiloxane of the above-mentioned formula (XIII) from the polyorganosiloxane of the above-mentioned formula (XVI) may be effected by the same method as that for the reduction reaction of converting the dinitro compound of the above-mentioned formula (XV) into the fluorine-containing diaminobenzene derivative of the present invention of the above-mentioned formula (I).

The polyimides of the present invention as produced by the above-mentioned reaction process, which have both a fluorine-containing group and a siloxane group and which have repeating units of the above-mentioned formulae (II), (III) and (IV), are characterized by having the repeating units of the above-mentioned formulae (III) and (IV). Therefore, the polyimides may be either binary copolymers having repeating units of only the above-mentioned formulae (III) and (IV) or ternary copolymers having repeating units of all the above-mentioned formulae (II), (III) and (IV). Anyhow, the polyimides of the present invention are necessary to have a molar ratio of the repeating unit of formula (II) of being from 0 to 98%, a molar ratio of the repeating unit of formula (III) of being from 1 to 99% and a molar ratio of the repeating unit of formula (IV) of being from 1 to 99%. However, it is more preferred that the polyimides of the present invention, which have a fluorine-containing group and a siloxane chain, have a molar ratio of the repeating unit of formula (III) of being from 5 to 60 mol % and a molar ratio of the repeating unit of formula (IV) of being from 20 to 80%, in order that the film to be formed from the polyimide may well have satisfactorily high water-repellent property and permeability. In the case, it is desired that the mean polymerization degree (m) of the polyorganosiloxane chain in the above-mentioned formula (IV) falls within the range of from 3 to 50. Additionally, in order that the polyimides of the present invention, which have a fluorine-containing group and a siloxane chain, may have a satisfactory capability of forming thin films and that the films to be formed from the polyimides may well have a sufficiently high strength, the polyimides are necessary to have a weight average molecular weight (as obtained, for example, by gel permeation chromatography) of 10,000 or more.

The liquid crystal-aligning agent of the present invention is coated on a transparent substrate, such as a transparent glass or plastic film substrate, as combined with a transparent electrode to form a polyimide resin film thereon, and thereafter the thus coated resin film is rubbed in a determined direction. In this way, it is used as aligning agent for liquid crystal cells. In using the liquid crystal-aligning agent of the present invention, the tilt angle of liquid crystal molecules may freely be controlled or adjusted by varying the molar ratio (b) of the repeating formula (VI) and/or the molar ratio (c) of the repeating unit of formula (VII) in the polyimide.

The method of obtaining polyimides to be used in the present invention is not specifically defined.

In general, they are obtained by reacting and polymerizing one or more compounds selected from tetracarboxylic acids of a general formula (XX):

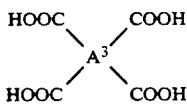

where $A^3$ represents a tetravalent organic group of constituting a tetracarboxylic acid, and four carbonyl groups as bonded to $A^3$ are directly bonded to different carbon atoms, and derivatives thereof, and a diamine of a general formula (XXI):

where $A^4$ represents a divalent organic group of constituting a diamine, and/or a diaminobenzene derivative of the above-mentioned formula (I), and/or a polyorganosiloxane of the above-mentioned formula (XIII) having a diaminophenyl group at one terminal thereof.

Specific examples of tetracarboxylic acids of the above-mentioned formula (XX) and derivatives thereof include aromatic tetracarboxylic acids, such as pyromellitic acid, 2,3,6,7-naphthalenetetracarboxylic acid, 1,2,5,6-naphthalenetetracarboxylic acid, 1,4,5,8-naphthalenetetracarboxylic acid, 2,3,6,7-anthracenetetracarboxylic acid, 1,2,5,6-anthracenetetracarboxylic acid, 3,3',4,4'-diphenyltetracarboxylic acid, bis(3,4-dicarboxyphenyl)ether, 3,3',4,4'-benzophenonetetracarboxylic acid, bis(3,4-dicarboxyphenyl)sulfone, bis(3,4-dicarboxyphenyl)methane, 2,2-bis(3,4-dicarboxyphenyl)propane, 1,1,1,3,3,3-hexafluoro-2,2-bis(3,4-dicarboxyphenyl)propane, bis(3,4-dicarboxyphenyl)dimethylsilane, bis(3,4-dicarboxyphenyl)diphenylsilane, 2,3,5,6-pyridinetetracarboxylic acid, and 2,6-bis(3,4-dicarboxyphenoxy)pyridine, and dianhydrides and dicarboxylic acid di-acid halides thereof; alicyclic tetracarboxylic acids, such as cyclobutanetetracarboxylic acid, cyclopentanetetracarboxylic acid, cyclohexanetetracarboxylic acid, and 3,4-dicarboxy-1,2,3,4-tetrahydro-1-naphthalenesuccinic acid, and dianhydrides and dicarboxylic acid di-acid halides thereof; and aliphatic tetracarboxylic acids such as butanetetracarboxylic acid, and dianhydrides and dicarboxylic acid di-acid halides thereof.

Tetracarboxylic acids of formula (XX) and derivatives thereof may be used singly or as a mixture of two or more of them.

Specific examples of diamine compounds of the above-mentioned formula (XXI) include aromatic diamines, such as m-diaminobenzene, p-diaminobenzene, 2,7-diaminonaphthalene, 2,6-diaminonaphthalene, 2,7-diaminoanthracene, 2,6-diaminoanthracene, 1,8-diaminoanthracene, 3,3'-diaminobiphenyl, 4,4'-diaminobiphenyl, 3,3'-diaminodiphenyl ether, 4,4'-diaminodiphenyl ether, 3,3'-diaminobenzophenone, 4,4'-diaminobenzophenone, 3,3'-diaminodiphenylsulfone, 4,4'-diaminodiphenylsulfone, 3,3'-diaminodiphenylsulfone, 4,4'-diaminodiphenylsulfide, 3,3'-diaminodiphenylmethane, 4,4'-diaminodiphenylmethane, 2,2-bis(3-aminophenyl)propane, 1,3-bis-(4-aminophenoxy)benzene, 1,4-bis(4-aminophenoxy)benzene, 4,4'-di(4-aminophenoxy)diphenylsulfone, 2,2'-bis[4-(4-aminophenoxy)phenyl]propane, 1,1,1,3,3,3-hexafluoro-2,2-bis(4-aminophenyl)propane, and 1,1,1,3,3,3-hexafluoro-2,2-bis[4-(4-aminophenoxy)phenyl]propane; as well as diaminosiloxanes, for example, as follows:

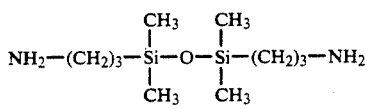

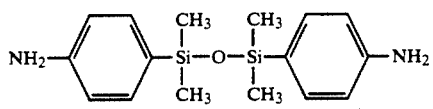

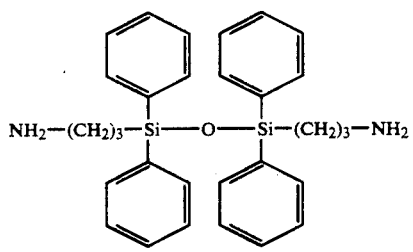

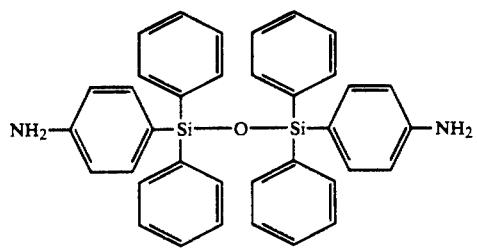

Additionally, other alicyclic diamines or aliphatic diamines may also be used in accordance with the object.

These diamines can be used singly or as a mixture of two or more of them.

The polyimides of the present invention, which have a fluorine-containing group and/or a siloxane chain in the side chain thereof and having repeating units of the above-mentioned formulae (V), (VI) and (VII), are produced from a diaminobenzene derivative of the above-mentioned formula (VI) and/or a diaminobenzene derivative of the above-mentioned formula (VII) by the method of condensation followed by imidation, which will be mentioned below.

As the tetracarboxylic acid of formula (XX) and its derivative, a tetracarboxylic acid dianhydride is generally used. Such a tetracarboxylic acid dianhydride is reacted and polymerized with a mixture comprising a fluorine-containing diaminobenzene derivative of formula (I) and/or a siloxane chain-containing diaminobenzene derivative of formula (XIII) and/or a diamine of formula (XXI) in an organic polar solvent to give a polyamide acid which is a polyimide intermediate. The reaction must satisfy the conditions of:

$$a+b+c=1$$

and $$0 \leq a < 1$$
$$0 \leq b < 1$$
$$0 \leq c < 1,$$

where a means a ratio of the number of mols of the diamine of formula (XXI) to the total number of mols of the diamine mixture used, b means a ratio of the number of mols of the fluorine-containing diaminobenzene derivative of formula (I) to the same, and c means a ratio of the number of mols of the siloxane chain-containing diaminobenzene derivative of formula (XIII) to the same. Precisely, the conditions indicate that the diamine of formula (XXI) is not always indispensable in the polyimides of the present invention, which are obtained by the reaction, but that the diaminobenzene of formula (I) and/or formula (XIII) are indispensable in them. More precisely, a may be 0; when b is 0, then $c>0$ necessarily; and when c is 0, then $b>0$ necessarily. b is 1 and both a and c may be 0; c is 1 and both a and b may be 0; but a and b may be 0; but a must not be 1, and both b and c must not be 0. The concrete combination of the repeating units are as follows.

a) a unit of formulae (V), (VI) and (VII),
b) a unit of formulae (V) and (VI),
c) a unit of formulae (V) and (VII),
d) a unit of formulae (VI),
e) a unit of formulae (VII) or
f) a unit of formulae (VI) and (VII)

One object of the present inventions to use the polyimides of the present as a liquid crystal-aligning agent so as to control the tilt angle of liquid crystal molecules on a substrate. The polyimides of the present invention are produced from starting materials of diaminobenzene derivatives of formula (I) and/or formula (XIII), so that they may elevate the tilt angle of liquid crystal molecules on a substrate when they are applied to the substrate. Accordingly, where c is 0, then $0<b\leq 1$ necessarily. In order to substantially elevate the tilt angle of liquid crystal molecules, it is desired to satisfy the condition of $0.01 \leq b \leq 1$. Where b is 0, then $0<c\leq 1$ necessarily, more preferabley $0.01 \leq c \leq 1$. When $b>0$ and $c>0$, then $(b+c)$ is desired to fall within the range of $0.01 \leq b+c \leq 1$. Where the values of b and/or c are larger, the tilt angle of liquid crystal molecules is to be larger. Accordingly, by adjusting the values of b and/or c, the tilt angle of liquid crystal molecules may be controlled within the range of from 1 degree to 90 degrees.

In general, the ratio of the number of total mols of the diamine mixture to the number of total mols of the tetracarboxylic acid dianhydride to be used in the polymerization falls within the range of from 0.5 to 1.5, more preferably from 0.8 to 1.2. In general, where the ratio is nearer to 1 (one), the molecular weight of the polymer to be obtained is larger, like an ordinary polycondensation reaction.

Where the polyimides of the present invention are used as a liquid crystal-aligning agent, the films to be formed therefrom are necessary to have a higher film strength than a determined one. In order to satisfy the requirement, the molecular weight of the polyimides of the present invention must substantially be 10,000 or more as a weight average molecular weight.

The intermediate polyamic acid is dehydrated under heat at 100° to 400° C. or is subjected to chemical imidation with a conventional imidating agent such as triethylamine/acetic anhydride to thereby give the intended fluorine and/or siloxane-containing polyimide of the present invention, which has repeating units of the above-mentioned formulae (V), (VI) and (VII).

Where the polyimides of the present invention thus produced are used as a liquid crystal-aligning agent, it is necessary to form a polyimide film having a thickness of from 200 to 3000 Å on a substrate as combined with a transparent electrode.

The method of forming such a polyimide film is not specifically defined.

In general, for example, a solution of a polyamic acid intermediate is directly coated on a substrate and heated thereon for imidation to form a polyimide film on the substrate.

As the solution of a polyamic acid intermediate to be used in the case, the above-mentioned polymer solution may directly be used; or alternatively, a polyamic acid intermediate as produced by the process mentioned above is put in a large amount of a poor solvent such as water or methanol, this is precipitated and recovered from the solvent and thus recovered precipitate may be re-dissolved in a solvent. The solvent to be used form forming the above-mentioned polymer solution of a polyamic acid intermediate and/or for redissolving the precipitated and recovered polyamic acid intermediate is not specifically defined, provided that it may dissolve the intended polyamic acid intermediate.

As specific examples of such solvents, there are mentioned N,N-dimethylformamide, N,N-dimethylacetamide, N-methylpyrrolidone, N-methylcaprolactam, dimethylsulfoxide, tetramethylurea, pyridine, dimethylsulfone, hexamethylphosphoramide, and γ-butyrolactone.

These solvents may be used either singly or as a combination of two or more of them.

Other solvents than the above-mentioned ones, which could not form a uniform solution when used singly, may also be used in combination of the above-mentioned solvent(s) only within such an amount that may form a uniform solution.

The temperature in the heating step for imidation of the polymer film as coated on a substrate may be selected from the range between 100° C. and 400° C., and especially preferably it is selected from the range between 150° C. and 350° C.

If the temperature for imidation is lower than 150° C., the imidation percentage would lower so that alignment of liquid crystal molecules as provided on the coated substrate would be unstable. On the other hand, if it is higher than 350° C., the coated film would color to yield a problem on display of liquid crystal cells.

Where the polyimides of the present invention are soluble in solvents, the polyamic acid intermediate to be obtained in accordance with the process mentioned above may directly be imidated in the form of its solution to give a solution of the resulting polyimide. In the case, the thus formed polyimide may be isolated from the solution and is again dissolved in any other pertinent solvent to give an intended polyimide solution.

Accordingly, the resulting polyimide solution may be coated on a substrate, whereupon the solvent is evaporated out to finally form an intended polyimide film on the substrate.

As mentioned above, a polyimide film having a thickness of from 200 to 3000 Å is formed on a transparent substrate, such as a transparent glass or plastic film substrate, as combined with a transparent electrode, and thereafter the film is rubbed. In this way, the polyimides of the present invention can be used as an aligning agent for liquid crystal cells.

As the fluorine-containing diaminobenzene derivatives of the present invention have a diamnophenyl group having a condensation reactivity, they may be reacted with any other condensing monomers by polycondensation because of the reactivity to give highly water-repelling high polymer compounds having an aromatic polyamide, polyamic acid or polyimide as the main chain moiety thereof and having a fluorine-containing group in the side chain thereof, with ease. Additionally, since the polyimides of the present invention having a fluorine-containing group and those having both a fluorine-containing group and a polysiloxane chain are novel polyimides which have high mechanical strength, heat-resistance and solvent-resistance, as characteristics of aromatic polyimides, and also have a high water-repelling property as a characteristic of the fluorine-containing group in the polymer, they can be applied to various fields where conventional polyimides have been used and also to other broader fields where conventional polyimides have not been used up to these days. Precisely, the novel polyimides of the present invention can be applied widely to protecting materials, insulating materials, adhesives, films, resist materials and construction materials in the field of electronic appliances and also to gas or liquid separation film materials in the other field. In particular, the polyimides of the present invention having both a fluorine-containing group and a polysiloxane chain are useful as novel gas or liquid separation film materials having high film strength, heat-resistance, solvent resistance and water-repelling property and also having high permeability and separation capacity. Accordingly, using films formed from the polyimides of the present invention having both a fluorine-containing group and a polysiloxane chain, separation of various gaseous mixtures or concentration of the separated gases, for example separation and concentration of oxygen from air or separation of hydrogen or carbon dioxide from air, as well as separation and concentration of an organic liquid from a water-containing organic liquid mixture may be effected extremely efficiently.

The polyimides of the present invention is useful as a liquid crystal-aligning agent capable of giving a large liquid crystal tilting angle.

Additionally, where the polyimides of the present invention is used as a liquid crystal-aligning agent, the liquid crystal tilting angle may well be controlled by varying the amounts of the repeating units having a fluorine-containing group and/or a siloxane chain in the polyimides.

Next, the present invention will be explained in more detail by way of the following Referential Examples, Working Examples, Experimental Examples and Use Examples, which, however, do not whatsoever restrict the scope of the present invention.

WORKING EXAMPLE 1

Production of Fluorine-containing Dinitrobenzene Derivative (1)

5.0 g (23 mmol) of 3,5-dinitrobenzyl chloride, 5.3 g (35 mmol) of 2,2,3,3,3-pentafluoro-1-propanol and 1.1 g (3.1 mmol) of tetrabutylammonium hydrogensulfate were dissolved in 50 ml of tetrahydrofuran, and a solution of 2.4 g (60 mmol) of sodium hydroxide as dissolved in 4 ml of water was added thereto and stirred overnight at room temperature. The reaction solution was extracted with diethyl ether, and the organic phase was taken out and dried with anhydrous sodium sulfate. The solvent was removed from the thus dried organic phase under reduced pressure to obtain a crude product, which was then purified by column chromatography with silica gel (using a developer of chloroform/hexane=1/1). As a result, 6.2 g of a fluorine-containing dinitrobenzene derivative having a structural formula of:

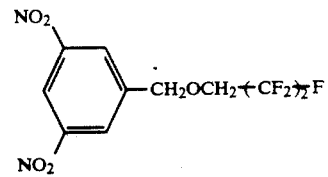

was obtained as an yellow oil. Yield: 81%.

The product was identified to have the above-mentioned structure by the following IR spectrum, $^1$H-NMR spectrum and elementary analysis data.

IR Spectrum (cm$^{-1}$): 3110(s), 2950(s), 2890(s), 1640(m), 1600(m), 1545(s, characteristic absorption by nitro group), 1470(m), 1344(s, characteristic absorption by nitro group), 1190(s, characteristic absorption by C—F bond), 1140(s, characteristic absorption by ether bond), 1100(s), 1025(s), 910(m), 810(m), 715(s).

$^1$H-NMR Spectrum, δ(CDCl$_3$, ppm): 4.30(t, 2H, —OCH$_2$CF$_2$—), 4.95(s, 2H, PhCH$_2$O—), 8.56 (d, 2H, peak of benzene ring), 8.96 (t, 1H, peak of benzene ring).

Elementary Analysis (%): C: 36.56, H: 2.04, N: 8.56 (calculated values: C: 36.38, H: 2.14, N: 8.48).

Next, 1.0 g (0.47 mmol) of 5% palladium-carbon powder (product by Japan Engelhard Co.) was dissolved in 20 ml of ethanol and hydrogen was introduced thereinto for 15 minutes so as to activate the catalyst. Afterwards, a solution of 5.0 g (15 mmol) of the fluorine-containing dinitrobenzene derivative as obtained by the above-mentioned reaction, as dissolved in 20 ml of ehtanol, was added to the thus activated catalyst solution, and the derivative was reduced for about 2 hours with introducing hydrogen into the reaction solution. After the catalyst was removed from the reaction solution by filtration, the solvent was concentrated under reduced pressure to obtain a crude product. This was then purified by column chromatography with silica gel (using a developer of ethyl acetate/hexane=1/1). As a result, 3.6 g of a fluorine-containing diaminobenzene derivative having a structural formula of:

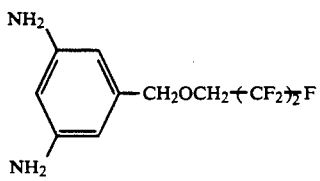

was obtained as a pale yellow oil. Yield: 88%.

The product was identified to have the above-mentioned structure by the following IR spectrum, $^1$H-NMR spectrum and elementary analysis data.

IR Spectrum (cm$^{-1}$): 3370(s, characteristic absorption by amino group), 3210(m), 2940(m), 2880(m), 1600(s), 1478(m), 1370(s, characteristic absorption by diaminophenyl group), 1190(s, characteristic absorption by C—F bond), 1150(s), 1120(s, characteristic absorption by ether bond), 1000(s), 1025(s), 980(w), 961(w), 935(w), 830(m).

$^1$H-NMR Spectrum, δ(CDCl$_3$, ppm): 3.50(bs, 4H,Ph-NH$_2$), 4.07(t, 2H, —OCH$_2$—CF$_2$—), 4.75(s, 2H, PhCH$_2$O—), 6.05(t, 1H, proton peak of benzene ring), 6.15 (d, 2H, proton peak of benzene ring).

Elementary Analysis (%): C: 44.93, H: 4.21, N: 10.24 (calculated values: C: 44.45, H: 4.10, N: 10.37).

WORKING EXAMPLE 2

Production of Fluorine-containing Dinitrobenzene Derivative (2)

The same reaction and purification as those in Working Example 1 were effected except that 9.1 g (35 mmol) of 1H,1H,2H,2H-nonafluoro-1-hexanol was used in place of 5.3 g (35 mmol) of 2,2,3,3,3-pentafluoro-1-propanol used in Working Example 1. As a result, 7.3 g of a fluorine-containing dinitrobenzene derivative having a structural formula of:

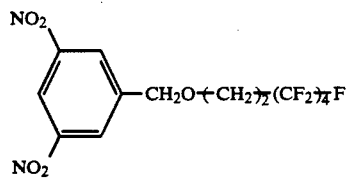

was obtained as an yellow oil. Yield: 75%.

The product was identified to have the above-mentioned structure by the following IR spectrum, $^1$H-NMR spectrum and elementary analysis data.

IR Spectrum (cm$^{-1}$): 3110(s), 2950(s), 2890(s), 1640(m), 1600(m), 1540(s, characteristic absorption by nitro group), 1470(m), 1344(s, characteristic absorption by nitro group), 1220(s, characteristic absorption by C—F bond), 1130(s, characteristic absorption by ether bond), 1000(m), 875(m), 805(m), 720(s).

$^1$H-NMR Spectrum, δ(CDCl$_3$, ppm): 2.60(m, 2H, —OCH$_2$CH$_2$CF$_2$—), 3.93 (t, 2H, —OCH$_2$CH$_2$CF$_2$—), 4.75(s, 2H, PhCH$_2$O—), 8.55 (d, 2H, proton peak of benzene ring), 8.96 (t, 1H, proton peak of benzene ring).

Elementary Analysis (%): C: 35.28, H: 1.97, N: 6.34 (calculated values: C: 35.15, H: 2.04, N: 6.31).

Next, 5.0 g (11 mmol) of the fluorine-containing dinitrobenzene derivative as obtained by the above-mentioned reaction was subjected to the same reduction and purification as those in Example 1. As a result, 3.3 g of a fluorine-containing diaminobenzene derivative having a structural formula of:

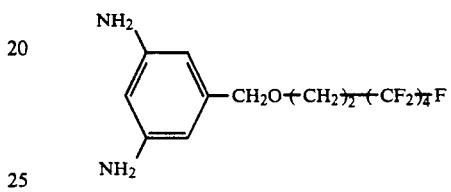

was obtained as a pale yellow oil. Yield: 78%.

The product was identified to have the above-mentioned structure by the following IR spectrum, $^1$H-NMR spectrum and elementary analysis data.

IR Spectrum (cm$^{-1}$): 3370(s, characteristic absorption by amino group), 3210(m), 2940(m), 2880(m), 1600(s), 1478(m), 1370(characteristic absorption by diaminophenyl group), 1220(s, characteristic absorption by C—F bond), 1150(s), 1125(s, characteristic absorption by ether bond), 1000(s), 1025(s), 980(w), 961(w), 935(w), 830(m).

$^1$H-NMR Spectrum, δ(CDCl$_3$, ppm): 2.48(m, 2H, —OCH$_2$CH$_2$CF$_2$—), 3.57(bs, 4H, Ph-NH$_2$), 3.79(t, 2H, —OCH$_2$CH$_2$CF$_2$—), 4.11(s, 2H, PhCH$_2$O), 6.01 (t, 1H, peak of benzene ring), 6.13(d, 2H, peak of benzene ring).

Elementary Analysis (%): C: 40.85, H: 3.37, N: 7.35 (calculated values: C: 40.64, H: 3.41, N: 7.29)

WORKING EXAMPLE 3

Production of Fluorine-containing Dinitrobenzene Derivative (3)

The same reaction and purification as those in Working Example 1 were effected except that 16 g (35 mmol) of 1H,1H,2H,2H-heptadecafluoro-1-decanol was used in place of 5.3 g (35 mmol) of 2,2,3,3,3-pentafluoro-1-propanol used in Working Example 1. As a result, 13.3 g of a fluorine-containing dinitrobenzene derivative having a structural formula of:

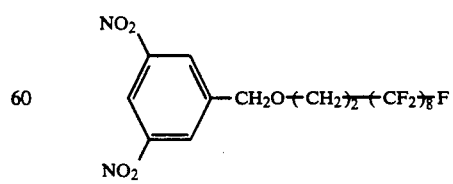

was obtained as an yellow oil. Yield: 90%.

The product was identified to have the above-mentioned structure by the following IR spectrum, $^1$H-NMR spectrum and elementary analysis data.

IR Spectrum (cm$^{-1}$): 3110(s), 2950(s), 2890(s), 1640(m), 1600(m), 1540(s, characteristic absorption by nitro group), 1470(m), 1340(s, characteristic absorption by nitro group), 1220(s, characteristic absorption by C—F bond), 1140(s, characteristic absorption by ether bond), 1000(m), 875(m), 805(m), 720(s).

$^1$H-NMR Spectrum, δ(CDCl$_3$, ppm): 2.60(m, 2H, —OCH$_2$CH$_2$CF$_2$—), 3.95(t, 2H, —OCH$_2$CH$_2$CF$_2$—), 4.74(s, 2H, PhCH$_2$O—), 8.53(d, 2H, proton peak of benzene ring), 8.97 (t, 1H, proton peak of benzene ring).

Elementary Analysis (%): C: 31.77, H: 1.44, N: 4.40 (calculated values: C: 31.69, H: 1.41, N: 4.35)

Next, 5.0 g (7.8 mmol) of the fluorine-containing dinitrobenzene derivative as obtained by the above-mentioned reaction was subjected to the same reduction and purification as those in Example 1. As a result, 3.1 g of a fluorine-containing diaminobenzene derivative having a structural formula of:

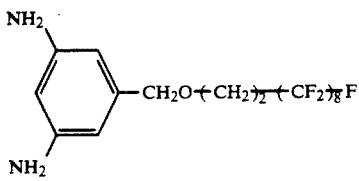

was obtained as a pale yellow oil. Yield: 61%.

The product was identified to have the above-mentioned structure by the following IR spectrum, $^1$H-NMR spectrum and elementary analysis data.

IR Spectrum (cm$^{-1}$): 3350(s, characteristic absorption by amino group), 3210(m), 2940(m), 2280(m), 1600(s), 1478(m), 1380(s, characteristic absorption by diamonphenyl group), 1220(s, characteristic absorption by C—F bond), 1150(s), 1130(s, characteristic absorption by ether bond), 1000(s), 1025(s), 980(w), 955(w), 935(w), 830(m).

$^1$H-NMR Spectrum, δ(CDCl$_3$, ppm): 2.47(m, 2H, —OCH$_2$CH$_2$CF$_2$—), 3.59 (bs, 4H, Ph-NH$_2$), 3.73(t, 2H, —OCH$_2$CH$_2$CF$_2$—), 4.35(s, 2H, PhCH$_2$O—), 6.01(t, 1H, peak of benzene ring), 6.12(d, 2H, peak of benzene ring).

Elementary Analysis (%): C: 35.01, H: 2.38, N: 4.66 (calculated values: C: 34.95, H; 2.24, N: 4.80)

WORKING EXAMPLE 4

Production of Fluorine-containing Polyimide (1)

0.7241 g (2.680 mmol) of the fluorine-containing diaminobenzene derivative as obtained in Working Example 1 and 1.1911 g (2.680 mmol) of 1,1,1,3,3,3-hexafluoro-2,2-bis(3,4-dicarboxyphenyl)Propane dianhydride, which had previously been purified by sublimation, were separately weighed and these were dissolved in 15 ml of anhydrous N,N-dimethylacetamide and stirred for one hour at 60° C. in an argon gas atmosphere for polycondensation. Next, the reaction solution was cooled to room temperature, and 3.32 ml (23.8 mmol) of triethylamine and 2.25 ml (23.8 mmol) of acetic anhydride were added thereto and heated up to 100° C. for effecting imidation for 30 minutes. The reaction solution was then poured into 800 ml of methanol so as to precipitate the polymer formed. The polymer thus formed was taken out by filtration and dried, to obtain 1.35 g of a fluorine-containing polyimide having a repeating unit of a formula:

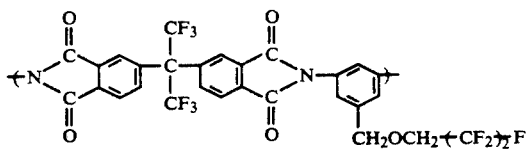

The molecular weight of the polymer thus obtained was measured by gel permeation chromatography. As a result, the number average molecular weight and the weight average molecular weight were $1.35 \times 10^4$ and $2.28 \times 10^4$, respectively, in polystyrene conversion.

The product was identified to have the above-mentioned structure by the following IR spectrum and $^1$H-NMR spectrum.

IR Spectrum (cm$^{-1}$): 2900(w), 1790(m), 1730(s, characteristic absorption by imido group), 1605(s), 1470(m), 1435(w), 1395(m), 1355(s, characteristic absorption by imido group), 1300(m), 1240(s), 1210(s, characteristic absorption by C—F bond), 1137(s), 1100(m, characteristic curve by ether bond), 990(w), 880(w), 850(w), 720(s), 630(w).

$^1$H-NMR Spectrum, δ(CDCl$_3$, ppm): 4.00(t, 2H, —OCH$_2$CF$_2$—), 4.80(s, 2H, PhCH$_2$O)—), 7.52(d, 2H, peak of benzene ring), 7.65(t, 1H, peak of benzene ring), 7.95 (m, 6H, peak of benzene ring).

WORKING EXAMPLE 5

Production of Fluorine-containing Polyimide (2)

0.6028 g (1.569 mmol) of the fluorine-containing diaminobenzene derivative as obtained in Working Example 2 and 0.6969 g (1.569 mmol) of 1,1,1,3,3,3-hexafluoro-2,2-bis(3,4-dicarboxyphenyl)propane dianhydride, which had previously been purified by sublimation, were separately weight and these were subjected to the same polycondensation, imidation and reprecipitation as those in Working Example 4. As result, 0.95 g of a fluorine-containing polyimide having a repeating unit of a formula:

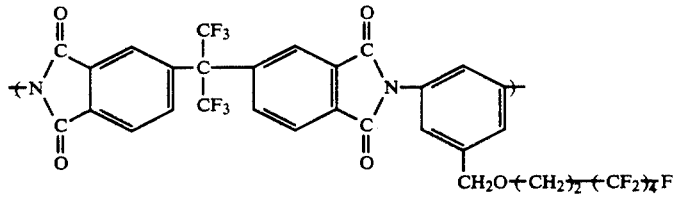

was obtained. The molecular weight of the polymer thus obtained was measured by gel permeation chromatography. As a result, the number average molecular weight and the weight average molecular weight were $1.15 \times 10^4$ and $2.20 \times 10^4$, respectively, in polystyrene conversion.

The product was identified to have the above-mentioned structure by the following IR spectrum and $^1$H-NMR spectrum.

IR Spectrum (cm$^{-1}$): 2900(w), 1790(m), 1730(s, characteristic absorption by imido group), 1605(s), 1470(m), 1435(w), 1395(m), 1355(s, characteristic absorption by imido group), 1300(m), 1240(s), 1210(s, characteristic absorption by C—F bond), 1137(s), 1100(m, characteristic curve by ether bond), 990(w), 880(w), 850(w), 720(s), 630(w).

$^1$H-NMR Spectrum, δ(CDCl$_3$, ppm): 2.44(m, 2H, —OCH$_2$CH$_2$CF$_2$—), 3.88(t, 2H, —OCH$_2$CH$_2$CF$_2$—), 4.71(s, 2H, PhCH$_2$O—), 7.53(d, 2H, peak of benzene ring), 7.64(t, 1H, peak of benzene ring), 8.00 (m, 6H, peak of benzene ring).

WORKING EXAMPLE 6

Production of Fluorine-containing Polyimide (3)

0.4438 g (1.155 mmol) of the fluorine-containing diaminobenzene derivative as obtained in Working Example 2, 1.0262 g (2.310 mmol) of 1,1,1,3,3,3-hexafluoro-2,2-bis(3,4-dicarboxyphenyl)propane dianhydride, which had previously been purified by sublimation, and 0.2313 g (1.155 mmol) of 4,4'-diaminodiphenyl ether were separately weighed and these were subjected to the same polycondensation, imidation and reprecipitation as those in Working Example 4. As a result, 1.25 g of a fluorine-containing polyimide having repeating units of formulae:

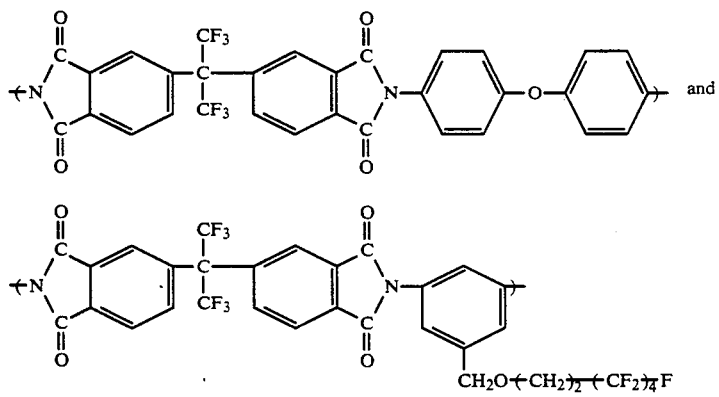

was obtained. The molecular weight of the polymer thus obtained was measured by gel permeation chromatography. As a result, the number average molecular weight and the weight average molecular weight were 3.45×10$^4$ and 5.21×10$^4$, respectively, in polystyrene conversion.

The product was identified to have the above-mentioned structure by the following IR spectrum and $^1$H-NMR spectrum. Additionally, the molar ratio of the above-mentioned repeating units in the product was obtained from the integral ratio of the proton peaks in its $^1$H-NMR spectrum to be 52/48 (mol %).

IR Spectrum (cm$^{-1}$): 2900(w), 1790(m), 1730(s, characteristic absorption by imido group), 1605(s), 1470(m), 1435(w), 1395(m), 1375(s, characteristic absorption by imido group), 1300(m), 1240(s), 1210(s, characteristic absorption by C—F bond), 1140(s), 1100(m, characteristic curve by ether bond), 990(w), 880(w), 830(w), 720(s), 630(w).

$^1$H-NMR Spectrum, δ(CDCl$_3$, ppm): 2.45(m, 2H, —OCH$_2$CH$_2$CF$_2$—), 3.88(t, 2H, —OCH$_2$CH$_2$CF$_2$—), 4.70(s, 2H, PhCH$_2$O—), 7.20 to 7.70(m, 11H, peak of benzene ring), 8.05 (m, 6H, peak of benzene ring).

REFERENTIAL EXAMPLE 1

Production of 3,5-Dinitrobenzyl Allyl Ether 20.0 g (101 mmol) of 3,5-dinitrobenzyl alcohol, 22 ml (254 mmol) of allyl bromide and 2.0 g (5.89 g) of tetrabutylamonium hydrogensulfate were dissolved in 100 ml of tetrahydrofuran, and a solution of 8.0 g (200 mmol) of sodium hydroxide as dissolved in 16 ml of water was added thereto and stirred overnight at room temperature. The reaction solution was extracted with diethyl ether and the organic phase was taken out and dried with anhydrous sodium sulfate. The solvent was removed under reduced pressure to obtain a crude product, which was then purified by column chromatography with silica gel (using a developer of chroroform/hexane=1/1). As a result, 19.1 g of 3,5-dinitrobenzyl allyl ether having a structural formula of:

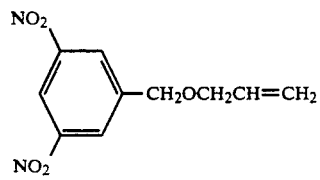

was obtained as a yellow oil. Yield: 80%. The product was identified to have the above-mentioned structure by the following IR spectrum, $^1$H-NMR spectrum and elementary analysis.

IR Spectrum (cm$^{-1}$): 3110(s), 2880(s), 1630(m), 1600(m), 1540(s, characteristic absorption by nitro group), 1470(m), 1345(s), characteristic absorption by nitro group), 1265(w), 1225(w), 1120(s, characteristic absorption by ether bond), 1075(s), 990(m), 910(m), 810(m), 758(m), 725(s).

$^1$H-NMR Spectrum, δ(CDCl$_3$, ppm): 4.17(d, 2H, —OCH$_2$CH=CH$_2$), 4.71 (s, 2H, PhCH$_2$O—), 5.35(m, 2H, —OCH$_2$CH=CH$_2$), 6.00(m, 1H, —OCH$_2$CH=CH$_2$), 8.54(d, 2H, peak of benzene ring), 8.94(t, 1H, peak of benzene ring).

Elementary Analysis (%): C: 50.40, H: 4.05, N: 11.47 (calculated values: C: 50.42, H: 4.24, N: 11.75)

REFERENTIAL EXAMPLE 2 to 4

Production of Hydrogen-monoterminated Polydimethylsiloxanes

Trimethylsilanol of the amount as indicated in Table 1 below was dissolved in 200 ml of dry tetrahydrofuran, and a hexane solution of an equimolar amount of n-butyl lithium was added thereto in an argon stream atmosphere. After stirred for 10 minutes, a solution of hexamethylcyclotrisiloxane of the amount also indicated in Table 1, as dissolved in 200 ml of dry tetrahydrofuran, was added thereto and stirred for 21 hours at room temperature. An excessive amount of dimethylchlorosilane was added to the reaction solution as a stopper to thereby stop the polymerization reaction. Next, the solvent was removed by distillation under reduced pressure, the salt as precipitated out was removed by filtration, and the resulting reaction mixture was heated at 120° C. for 3 hours in vacuum of 0.1 mmHg or less to remove the non-reacted cyclosiloxane and the excessive stopper therefrom. As a result, a hydrogen-monoterminated polydimethylsiloxane having a structural formula of:

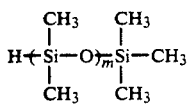

was obtained as a colorless transparent viscous liquid.

The thus obtained hydrogen-monoterminated polydimethylsiloxane and the 3,5-dinitrobenzyl allyl ether (about 1.2 molar times) as obtained in Referential Example 1 were dissolved in 50 ml of toluene and heated at 80° C. in an argon stream atmosphere, and thereafter 100 μl of isopropanol solution (0.1 mol/liter) of chloroplatinic acid (H$_2$PtCl$_6$·6H$_2$O) was added thereto and stirred for about 4 hours. The solvent was removed by distillation under reduced pressure to obtain a crude product, which was then purified by column chromatography with silica gel (using a developer of diethyl ether/hexane = 1/8). As a result, a polydimethylsiloxane having a dinitrophenyl group at one terminal thereof and having a structural formula of:

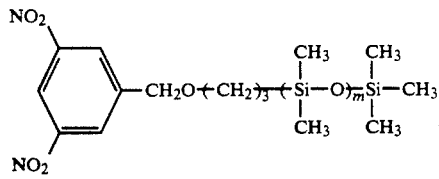

was obtained as a pale yellow oil.

Next, 5.0 g of 5% palladium-carbon powder (product by Japan Engelhard Co.) was dissolved in 50 ml of ethanol and hydrogen was introduced thereinto for 15 minutes so as to activate the catalyst. Afterwards, a solution of the hydropolydimethylsiloxane having a dinitrophenyl group at one terminal thereof, which had been obtained by the above-mentioned reaction, as dissolved in 50 ml of ethanol was added to the thus activated catalyst solution, and the polymer was reduced for about 2 hours with introducing hydrogen into the reaction solution. After the catalyst was removed from the reaction solution by filtration, the solvent was concentrated under reduced pressure to obtain a crude product. This was then purified by column chromatography with silica gel (using a developer of ethyl acetate/hexane = 1/1). As a result, a hydropolydimethylsiloxane having a diaminophenyl group at one terminal thereof and having a structural formula of:

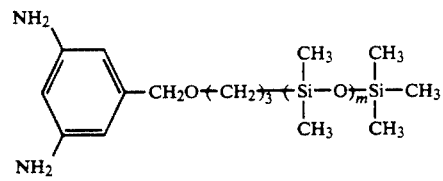

was obtained as colorless transparent viscous liquid. The product was identified to have the above-mentioned structure by the following IR spectrum, $^1$H-NMR spectrum and elementary analysis data. The yield of the polysiloxane thus obtained as well as the value of the average degree of polymerization (m) as obtained from the ratio of the peak areas of the $^1$H-NMR spectrum are shown in Table 1 below.

IR Spectrum (cm$^{-1}$): 3370(s, characteristic absorption by amino group), 2950(m), 2860(m), 1600(s), 1530(s), 1470(m), 1350(s, characteristic absorption by diaminophenyl group), 1250(s, characteristic absorption by Si—C bond), 1190(s), 1000 to 1100 (s, characteristic absorption by Si—O—Si bond), 840(m).

$^1$H-NMR Spectrum, δ(CDCl$_3$, ppm): 0.10(s, Si—CH$_3$), 0.89(t, —OCH$_2$CH$_2$CH$_2$Si—), 1.63(m, —OCH$_2$CH$_2$CH$_2$Si—), 3.43 (t, —OCH$_2$CH$_2$CH$_2$Si—), 3.58(bs, Ph-NH$_2$), 4.35(s, PhCHCO$_2$O—), 5.98 (t, peak of benzene ring), 6.13 (d, peak of benzene ring).

TABLE 1

| No. of Referential Example | Amount (g) of Trimethylsilanol | Amount (g) of hexamethylcyclotrisiloxane | Yield (g) | Average Degree of Polymerization (m) |
| --- | --- | --- | --- | --- |
| 2 | 2.00 | 9.86 | 9.22 | 7.7 |
| 3 | 1.00 | 7.40 | 6.54 | 10.3 |
| 4 | 1.00 | 9.86 | 8.89 | 13.5 |

WORKING EXAMPLE 7

Production of Polyimide Having Fluorine-containing Group and Siloxane Chain (1)

0.5837 g (1.519 mmol) of the fluorine-containing diaminobenzene derivative as obtained in Working Example 2, 0.4880 g (0.5926 mmol) of the polydimethylsiloxane having a diaminophenyl group at one terminal thereof, as obtained in Referential Example 2, and 0.9381 g (2.112 mmol) of 1,1,1,3,3,3-hexafluoro-2,2-bis(3,4-dicarboxyphenyl)propane dianhydride, which had previously been purified by sublimation, were separately weighed and subjected to the same polycondensation, imidation and re-precipitation as those in Working Example 4. As a result, 1.19 g of a polyimide having a fluorine-containing group and a siloxane chain and having repeating units of:

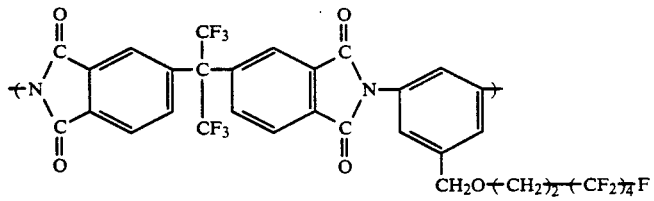

and

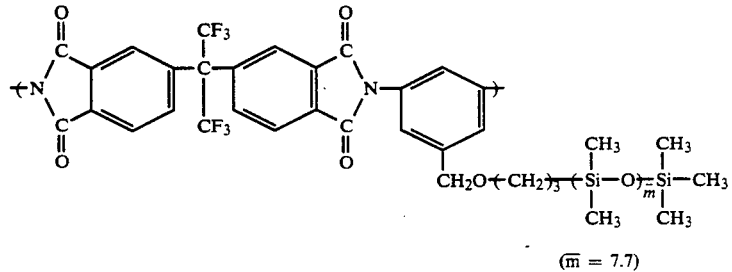

($\overline{m}$ = 7.7)

was obtained. The molecular weight of the polymer thus obtained was measured by gel permeation chromatography. As a result, the number average molecular weight and the weight average molecular weight were $1.67 \times 10^4$ and $3.06 \times 10^4$, respectively, in polystyrene conversion. The product was identified to have the above-mentioned structure by the following IR spectrum and $^1$H-NMR spectrum. Additionally, the molar ratio of the above-mentioned repeating units in the product was obtained from the integral ratio of the proton peaks in its $^1$H-NMR spectrum to be 70/30 (mol %).

IR Spectrum (cm$^{-1}$): 3080(m), 2950(s), 1780(m), 1710(s, characteristic absorption by imido group), 1595(s), 1500(s), 1470(m), 1435(w), 1395(m), 1380(s, characteristic absorption by imido group), 1300(m), 1260(s, characteristic absorption by Si—C bond), 1210(s, characteristic absorption by C—F bond), 1000 to 1100(s, characteristic absorption by Si—O—Si bond), 880(m), 840(S), 700(m).

$^1$H-NMR Spectrum, $\delta$(CDCl$_3$, ppm): 0.10(s, Si—CH$_3$), 0.62(t, —OCH$_2$CH$_2$CH$_2$Si—), 1.70(m, —OCH$_2$CH$_2$CH$_2$Si—), 2.47(m, OCH$_2$CH$_2$CF$_2$—), 3.51(t, —OCH$_2$CH$_2$CH$_2$Si—), 3.75(t, OCH$_2$CH$_2$CF$_2$—), 4.70, 4.65(s, PhCH$_2$O—), 7.63(m, peak of benzene ring), 8.08 (m, peak of benzene ring).

WORKING EXAMPLE 8

Production of Polyimide Having Fluorine-containing Group and Siloxane Chain (2)

0.8741 g (2.275 mmol) of the fluorine-containing diaminobenzene derivative as obtained in Working Example 2, 2.3111 g (2.2726 mmol) of the polydimethylsiloxane having a diaminophenyl group at one terminal thereof, as obtained in Referential Example 2, 3.0298 g (6.820 mmol) of 1,1,1,3,3,3-hexafluoro-2,2-bis(3,4-dicarboxyphenyl)propane dianhydride, which had previously been purified by sublimation, and 0.4551 g (2.2726 mmol) of 4,4'-diaminodiphenyl ether were separately weighed and subjected to the same polycondensation, imidation and re-precipitation as those in Working Example 4. As a result, 5.21 g of a polyimide having a fluorine-containing group and a siloxane chain and having repeating units of:

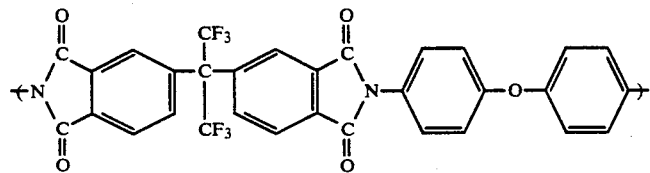

and

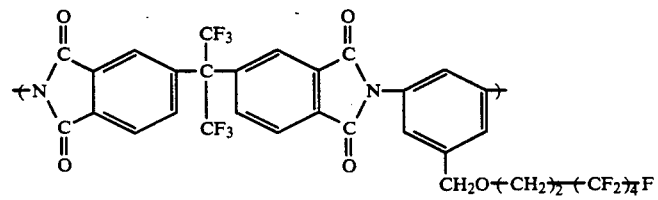

and

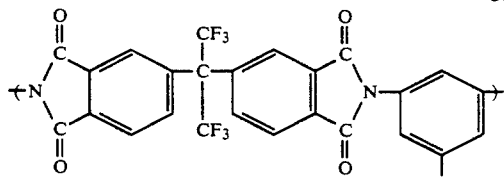

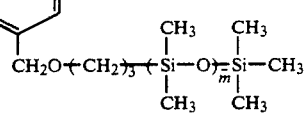

($\overline{m}$ = 7.7)

was obtained. The molecular weight of the polymer thus obtained was measured by gel permeation chromatography. As a result, the number average molecular weight and the weight average molecular weight were $5.37 \times 10^4$ and $8.03 \times 10^4$, respectively, in polystyrene conversion. The product was identified to have the above-mentioned structure by the following IR spectrum and $^1$H-NMR spectrum. Additionally, the molar ratio of the above-mentioned repeating units in the product was obtained from the integral ratio of the proton peaks in its $^1$H-NMR spectrum to be 40/31/29 (mol %).

IR Spectrum (cm$^{-1}$): 3080(m), 2950(s), 1780(m), 1710(s, characteristic absorption by imido group), 1595(s), 1500(s), 1470(m), 1435(w), 1395(m), 1375(s, characteristic absorption by imido group), 1300(m), 1260(s, characteristic absorption by Si—C bond), 1210(s, characteristic absorption by C—F bond), 1000 to 1100(s, characteristic absorption by Si—O—Si bond), 880(m), 840(s), 700(m).

$^1$H-NMR Spectrum, δ(CDCl$_3$, ppm): 0.10(s, Si—CH$_3$), 0.58(t, —OCH$_2$CH$_2$CH$_2$Si—), 1.70(m, —OCH$_2$CH$_2$CH$_2$Si—), 2.47(m, OCH$_2$CH$_2$CF$_2$—), 3.51 (t, —OCH$_2$CH$_2$CH$_2$Si—), 3.75 (t, OCH$_2$CH$_2$CF$_2$—), 4.70, 4.65 (s, PhCH$_2$O—), 7.20(d, peak of benzene ring), 7.41(d, peak of benzene ring), 7.55(m, peak of benzene ring), 7.80 to 8.10 (m, peak of benzene ring).

WORKING EXAMPLE 9

Production of Polyimide Having Fluorine-containing Group and Siloxane Chain (3)

0.3115 g (0.533 mmol) of the fluorine-containing diamnobenzene derivative as obtained in Working Example 3, 1.0846 g (1.066 mmol) of the polydimethylsiloxane having a diaminophenyl group at one terminal thereof, as obtained in Referential Example 3, 1.1839 g (2.665 mmol) of 1,1,1,3,3,3-hexafluoro-2,2-bis(3,4-dicarboxyphenyl)propane dianhydride, which had previously been purified by sublimation, and 0.2135 g (1.066 mmol) of 4,4'-diaminodiphenyl ether were separately weighed and subjected to the same polycondensation, imidation and re-precipitation as those in Working Example 4. As a result, 2.09 g of a polyimide having a fluorine-containing group and a siloxane chain and having repeating units of:

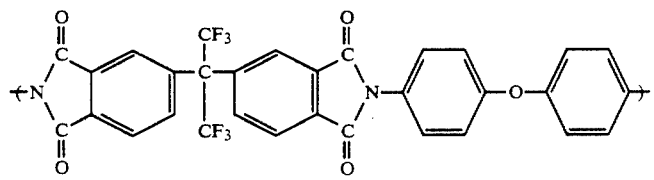

and

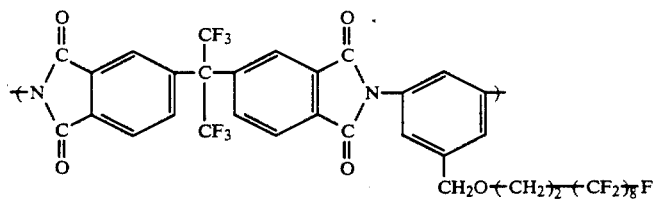

and

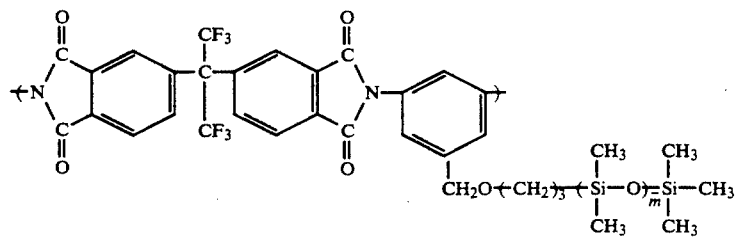

($\overline{m}$ = 10.3)

was obtained. The molecular weight of the polymer thus obtained was measured by gel permeation chromatography. As a result, the number average molecular weight and the weight average molecular weight were $3.12 \times 10^4$ and $4.81 \times 10^4$, respectively, in polystyrene conversion. The positions of peaks in IR spectrum and $^1$H-NMR spectrum of the product were same as those of the product in Working Example 8. Additionally, the molar ratio of the above-mentioned repeating units in the product was obtained from the integral ratio of the proton peaks in its $^1$H-NMR spectrum to be 47/22/31 (mol %).

WORKING EXAMPLE 10

Production of Polyimide Having Fluorine-containing Group and Siloxane Chain (4)

0.2506 g (0.4285 mmol) of the fluorine-containing diaminobenzene derivative as obtained in Working Example 3, 2.000 g (1.714 mmol) of the polydimethylsiloxane having a diaminophenyl group at one terminal thereof, as obtained in Referential Example 4, 1.335 g (3.000 mmol) of 1,1,1,3,3,3-hexafluoro-2,2-bis(3,4-dicarboxyphenyl)propane dianhydride, which had previously been purified by sublimation, and 0.1716 g (0.8570 mmol) of 4,4'-diaminodiphenyl ether were separately weighed and subjected to the same polycondensation, imidation and re-precipitation as those in Working Example 4. As a result, 3.26 g of a polyimide having a fluorine-containing group and a siloxane chain and having repeating units of:

the product was obtained from the integral ratio of the proton peaks in its $^1$H-NMR spectrum to be 32/16/52 (mol %).

REFERENTIAL EXAMPLE 5

Production of Polyimide Homopolymer 1,1,1,3,3,3-hexafluoro-2,2-bis(3,4-dicarboxyphenyl)-propane dianhydride and 4,4'-diaminodiphenyl ether were weighed each in an equimolar amount and subjected to the same polycondensation, imidation and re-precipitation as those in Working Example 4. As a result, a polyimide homopolymer having a repeating unit of:

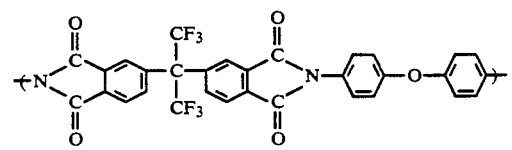

was obtained.

EXPERIMENTAL EXAMPLE

Measurement of Surface Contact Angle

The polyimide homopolymer as obtained in Referential Example 5 and the polymers obtained in Working Example 4 to 10 were weighed each in an amount of 300

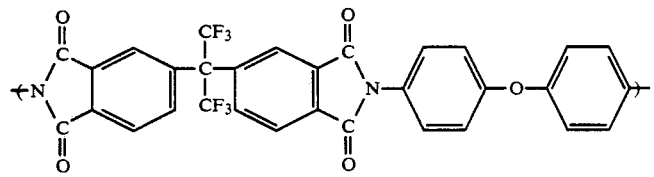

and

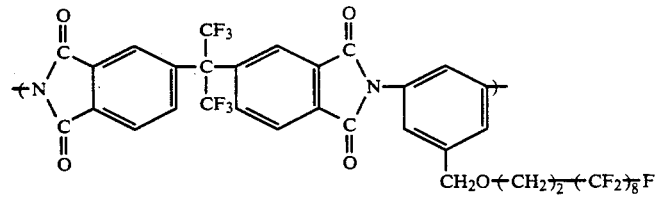

and

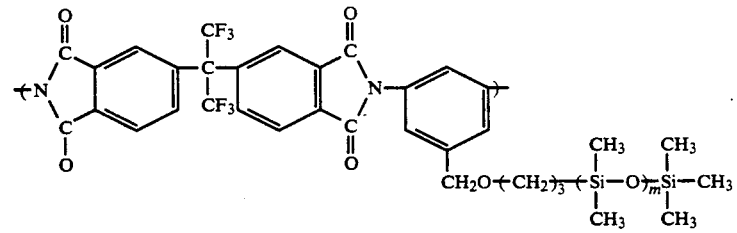

(m = 13.5)

was obtained. The molecular weight of the polymer thus obtained was measured by gel permeation chromatography. As a result, the number average molecular weight and the weight average molecular weight were $1.16 \times 10^5$ and $2.17 \times 10^5$, respectively, in polystyrene conversion. The positions of peaks in IR spectrum and $^1$H-NMR spectrum of the product were same as those of the product in Working Example 8. Additionally, the molar ratio of the above-mentioned repeating units in mg, and each of them was dissolved in a mixed solvent of tetrahydrofuran/toluene (3/1) and spread over a Teflon plate having a size of 5 cm × 5 cm. After the solvent was removed by gradually vaporizing it, a homogeneous film having a thickness of about 80 μm was formed on the plate. A water drop was dropped down on each of the thus formed films and the contact angle of the water drop to the surface of the film was measured with a contact angle-measuring device. The results obtained are shown in Table 2 below. In Table 2, the value of the surface contact angle to the film from the polyimide homopolymer is shown as Referential Example 1.

TABLE 2

| Sample Film | Contact Angle (degree) with Water |
|---|---|
| Comparative Example 1 | 81 |
| Working Example 4 | 92 |
| Working Example 5 | 96 |
| Working Example 6 | 97 |
| Working Example 7 | 101 |
| Working Example 8 | 100 |
| Working Example 9 | 115 |
| Working Example 10 | 124 |

As is obvious from the results in Table 2 above, the films as formed from the fluorine-containing polyimides and polyimides having both a fluorine-containing group and a polysiloxane chain of the present invention had a water contact angle of more than 90 degrees. Accordingly, these were verified to have a high water-repelling property.

USE EXAMPLE 1

Gas Permeability Coefficient

The gas permeability coefficients of each of the film samples as formed from the polyimide homopolymer of Referential Example 5 and from the polyimides of Working Examples 8 to 10 were measured with respect to various gases as indicated in Table 3 below (nitrogen, oxygen, carbon dioxide, hydrogen and methane), by means of an ordinary vacuum pressure method. The results obtained are shown in Table 3. In Table 3, the values of gas permeability coefficients of the film from the polyimide homopolymer are shown as Referential Example 1.

TABLE 3

| Sample Film | Gas Permeability Coefficient* × $10^9$ | | | | |
|---|---|---|---|---|---|
| | Nitrogen | Oxygen | Carbon Dioxide | Hydrogen | Methane |
| Comparative Example 1 | 0.0222 | 0.115 | 0.714 | 2.52 | 0.0134 |
| Working Example 8 | 3.01 | 8.02 | 21.9 | 24.2 | 15.4 |
| Working Example 9 | 4.41 | 10.7 | 61.6 | 28.5 | 22.5 |
| Working Example 10 | 8.06 | 20.9 | 121 | 55.8 | 49.5 |

*unit: $cm^2$ (STP) · $cm/cm^2$ · sec · cmHg

As is obvious from the results in Table 3 above, the films formed from the polyimides of the present invention having both a fluorine-containing group and a polysiloxane chain all had a much higher gas permeability than the film formed from the comparative polyimide homopolymer.

USE EXAMPLE 2

Pervaporation

The film of Working Example 10, as formed in the previous Experimental Example, was set in a stainless steel pervaporation cell and subjected to pervaporation test using an aqueous solution of an organic liquid of a low concentration at 50° C., where the chamber into which a vapor is permeated through the film had a reduced pressure of about 0.1 mmHg. The vapor as permeated through the film was recovered with a liquid nitrogen trap. From the weight of the thus trapped vapor, the permeability coefficient (P) was obtained after correction with respect to the film thickness. The composition of the permeated vapor was analyzed by gas chromatography. Accordingly, the separation coefficient α(organic liquid/water) was obtained from the following formula. The results obtained are shown in Table 4 below. α(organic liquid/water)=[(weight proportion of organic liquid in the permeated liquid/(weight proportion of water in the permeated liquid)]/[(weight proportion of organic liquid in the fed liquid)/(weight proportion of water in the fed liquid)]

TABLE 4

| Organic Liquid | Concentration of Organic Liquid (wt. %) | | α(organic liquid/water) | P (g · m/$m^2$ · h) |
|---|---|---|---|---|
| | Fed Liquid | Permeated Liquid | | |
| Ethanol | 6.26 | 29.5 | 6.27 | $1.05 \times 10^{-2}$ |
| 2-Propanol | 5.47 | 30.8 | 7.69 | $1.52 \times 10^{-2}$ |
| Acetonitrile | 5.92 | 62.7 | 26.7 | $2.25 \times 10^{-2}$ |
| Acetone | 6.27 | 62.7 | 25.1 | $2.35 \times 10^{-2}$ |
| Tetrahydrofuran | 6.73 | 73.2 | 37.9 | $6.43 \times 10^{-2}$ |

As is obvious from the results in Table 4 above, the film as formed form the polyimide of the present invention having both a fluorine-containing group and a polysiloxane chain is useful as a film material for highly selectively separating organic liquids from various organic liquid-containing aqueous solutions.

WORKING EXAMPLE 11

0.058 g (0.1 mmol) of the following compound:

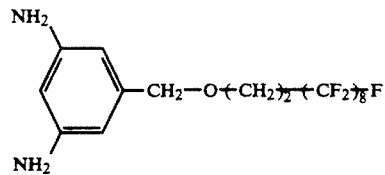

as a fluorine-containing diaminobenzene derivative, 0.779 g (1.9 mmol) of 2,2-bis[4-(4-aminophenoxy)-phenyl]propane (hereinafter referred to as BAPB) as a diamine, and 0.39 g (2.00 mmol) of 1,2,3,4-cyclobutanetetracarboxylic acid dianhydride (hereinafter referred to as CBDA) were dissolved in 7.5 g of N-methylphyrrolidone (hereinafter referred to as NMP) and stirred for 4 hours at 20° C. for polycondensation to prepare a solution of a polyamic acid intermediate.

The molecular weight of the polymer thus obtained was measured by gel permeation chromatography. As a result, the polymer had a weight average molecular weight of $1.1 \times 10^5$ in polyethylene glycol conversion.

The solution was diluted with NMP to a concentration of 4% by weight, and the diluted solution was then coated over a transparent electrode-having glass substrate by spin-coating at 3500 rpm and heat-treated at 180° C. for 60 minutes to form a uniform polyimide film on the substrate.

The coated film was rubbed with a cloth, and two substrates thus coated and rubbed were combined via a 50 μm-spacer therebetween with the rubbing direction of the two substrates being in parallel to each other. Then, a liquid crystal (ZLI-2293, product by Merk Co.) was introduced into the combined substrates to form a cell as homogeneously aligned.

The cell was rotated in cross nicol, whereupon distinct light and darkness was admitted. Accordingly, it was ascertained that the liquid crystal being between the two rubbed substrates was well aligned to the rubbing direction.

The tilt angle of the cell was measured by a crystal rotation mehtod to be 4.3 degrees.

WORKING EXAMPLE 12

A solution of a different polyamic acid intermediate was prepared in the same manner as in Working Example 11, except that 0.117 g (0.2 mmol) of a fluorine-containing diaminobenzene derivative of the following formula:

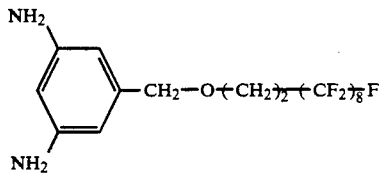

0.738 g (1.8 mmol) of BAPB as a diamine, 0.39 g (2.0 mmol) of CBDA as an acid anhydride, and 7.1 g of NMP were used.

The molecular weight of the polymer thus obtained was measured by gel permeation chromatography. As a result, the polymer had a weight average molecular weight of $1.1 \times 10^5$ in polyethylene glycol conversion.

Next, a cell was prepared in the same manner as in Working Example 11 except that the polyamic acid intermediate solution prepared above was used. After this was rotated in a cross nicol, distinct light and darkness was admitted. Accordingly, it was ascertained that the liquid crystal being between the two rubbed substrates was well aligned to the rubbing direction.

The tilt angle of the cell was measured by a crystal rotation method to be 10 degrees.

WORKING EXAMPLE 13

A solution of a different polamic acid intermediate was prepared in the same manner as in Working Example 11, except that 0.23 g (0.4 mmol) of a fluorine-containing diamnobenzene derivative of the following formula:

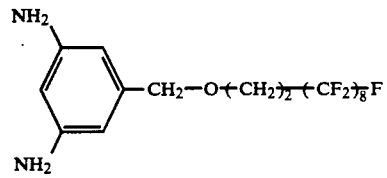

0.66 g (1.6 mmol) of BAPB as a diamine, 0.39 g (2.0 mmol) of CBDA as an acid anhydride, and 7.3 g of NMP were used.

The molecular weight of the polymer thus obtained was measured by gel permeation chromatography. As a result, the polymer had a weight average molecular weight of $6.0 \times 10^4$ in polyethylene glycol conversion.

Next, a cell was prepared in the same manner as in Working Example 11 except that the polyamic acid intermediate solution prepared above was used. The tilt angle of the cell was measured by a crystal rotation method. In the case, however, the tilt angle was found to be higher than the critical limitation of 15 degrees measurable by the crystal rotation method.

The cell was observed with a polarizing microscope, whereupon a distinct isogyre was seen in the vicinity of the center of the visual field. Accordingly, the tilt angle was found to be almost 90 degrees.

WORKING EXAMPLE 14

A solution of a different polyamic acid intermediate was prepared in the same manner as in Working Example 11, except that 0.31 g (0.8 mmol) of a fluorine-containing diaminobenzene derivative of the following formula:

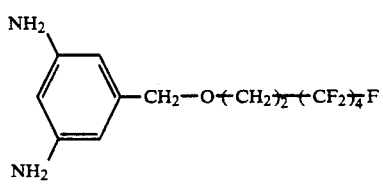

was used in place of the fluorine-containing diaminobenzene derivative of Working Example 11, that 0.49 g (1.2 mmol) of BAPB was used as a diamine, that 0.39 g (2.0 mmol) of CBDA was used as an acid anhydride, and that 6.7 g of NMP was used as a solvent.

The molecular weight of the polymer thus obtained was measured by gel permeation chromatography. As a result, the polymer had a weight average molecular weight of $9.5 \times 10^4$ in polyethylene glycol conversion.

Next, a cell was prepared in the same manner as in Working Example 11 except that the polyamic acid intermediate solution prepared above was used. After this was rotated in a cross nicol, distinct light and darkness was admitted. Accordingly, it was ascertained that the liquid crystal being between the two rubbed substrates was well aligned to the rubbing direction.

The tilt angle of the cell was measured by a crystal rotation method to be 9.8 degrees.

WORKING EXAMPLE 15

A solution of a different polyamic acid intermediate was prepared in the same manner as in Working Example 11, except that 0.082 g (0.1 mmol) of a silicone chain-containing diaminobenzene derivative of the following formula:

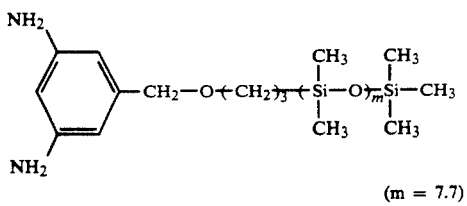

(m = 7.7)

was used in place of the fluorine-containing diaminobenzene derivative of Working Example 11, that 0.779 g (0.1 mmol) of BAPB was used as a diamine, that 0.39 g (2.0 mmol) of CBDA was used as an acid anhydride, and that 7.1 g of NMP was used as a solvent.

The molecular weight of the polymer thus obtained was measured by gel permeation chromatography. As a result, the polymer had a weight average molecular weight of $1.0 \times 10^5$ in polyethylene glycol conversion.

Next, a cell was prepared in the same manner as in Working Example 11 except that the polyamic acid intermediate solution prepared above was used. After this was rotated in a Cross Nicol, distinct light and darkness was admitted. Accordingly, it was ascertained that the liquid crystal being between the two rubbed substrates was well aligned to the rubbing direction.

The tilt angle of the cell was measured by a crystal rotation method to be 8.2 degrees.

WORKING EXAMPLE 16

0.87 g (2.28 mmol) of a fluorine-containing diaminobenzene derivative of the following formula:

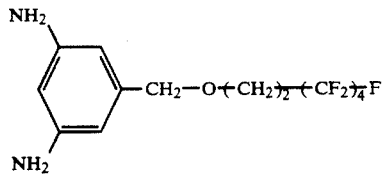

2.31 g (2.27 mmol) of a silicone chain-containing diaminobenzene derivative of the following formula:

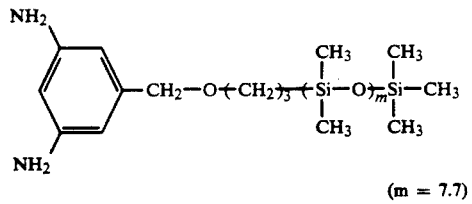

(m = 7.7)

0.46 g (2.27 mmol) of diaminodiphenyl ether (hereinafter referred to as DDE) as a diamine, and 3.03 g (6.82 mmol) of 1,1,1,3,3,3-hexafluoro-2,2-bis(3,4-dicarboxyphenyl)propane dianhydride (hereinafter referred to as 6FDA) as an acid anhydride were dissolved in 43.3 g of N,N-dimethylacetamide and stirred for 1 hour at 60° C. for polycondensation to obtain a solution of a polyamic acid intermediate.

Next, after the solution was cooled to room temperature, 3.32 ml (23.8 mmol) of triethylamine and 2.25 ml (23.8 mmol) of acetic anhydride were added thereto for effecting imidation at 100° C. for 30 minutes. The reaction solution was then put in 800 ml of methanol, and the white precipitate thus formed was taken out by filtration and dried to obtain a white polyimide powder.

The molecular weight of the polymer thus obtained was measured by gel permeation chromatography. As a result, the polymer had a weight average molecular weight of $8.03 \times 10^4$ in polystyrene conversion.

1.0 g of the powder was dissolved in 24 g of NMP to form a solution having a concentration of the total solid content of being 4% by weight. The resulting solution was coated over a transparent electrode-having glass substrate by spin-coating at 3500 rpm and heat-treated at 180° C. for 60 minutes to form a uniform polyimide coat on the substrate.

Next, a cell was prepared in the same manner as in Working Example 11, using the thus coated substrates, and the tilt angle of the cell was measured by a crystal rotation method. In the case, however, the tilt angle was found to be higher than the critical limitation of 15 degrees measurable by the crystal rotation method.

The cell was observed with a polarizing microscope, whereupon a distinct isogyre was seen in the vicinity of the center of the visual field. Accordingly, the tilt angle was found to be almost 90 degrees.

WORKING EXAMPLE 17

A solution of a different polyamic acid intermediate was prepared in the same manner as in Working Example 11, except that 0.12 g (0.2 mmol) of a fluorine-containing diaminobenzene derivative of the following formula:

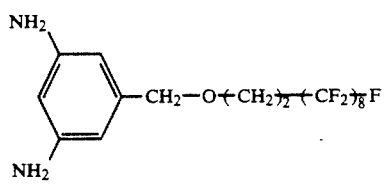

0.74 g (1.8 mmol) of BAPB as a diamine, and 0.60 g (2.0 mmol) of 3,4-dicarboxy-1,2,3,4-tetrahydro-1-naphthalenesuccinic acid anhydride (hereinafter referred to as TDA) as an acid anhydride were used. 0.9 ml (12 mmol) of pyridine and 0.9 ml (20 mmol) of acetic anhydride were added to the solution, which was then subjected to imidation at 50° C. for 3 hours. The reaction solution was put in 500 ml of methanol, and the white precipitate formed was taken out by filtration and dried to obtain a white polyimide powder.

The molecular weight of the polymer thus obtained was measured by gel permeation chromatography. As a result, the polymer had a weight average molecular weight of $5.0 \times 10^4$ in polyethylene glycol conversion.

1.0 g of the powder was dissolved in 24 g of γ-butyrolactone to form a solution having a concentration of the total solid content of being 4% by weight, and the resulting solution was coated on a transparent electrode-having glass substrate by spin-coating at 3500 rpm and heat-treated at 180° C. for 60 minutes to form a uniform polyimide film on the substrate.

Next, using the thus coated substrates, a cell was prepared in the same manner as in Working Example 11, and this was rotated in a cross nicol, whereupon distinct light and darkness was admitted. Accordingly, it was ascertained that the liquid crystal being between the two rubbed substrates was well aligned to the rubbing direction.

The tilt angle of the cell was measured by a crystal rotation method to be 1.5 degrees.

COMPARATIVE EXAMPLE 2

A solution of a comparative polyamic acid intermediate was prepared in the same manner as in Working Example 11, except that the fluorine-containing diaminobenzene derivative was not used but 2.05 g (5.0 mmol) of BAPB, 0.97 g (4.93 mmol) of CBDA and 17.1 g of NMP were used.

The molecular weight of the polymer thus obtained was measured by gel permeation chromatography. As a result, the polymer had a weight average molecular weight of $9.4 \times 10^4$ in polyethylene glycol conversion.

Next, a cell was prepared also in the same manner as in Working Example 11, except that the polymer prepared above was used. The tilt angle of the cell was measured by a crystal rotation method to be 2.5 degrees.

COMPARATIVE EXAMPLE 3

A comparative white polyimide powder was prepared in the same manner as in Working Example 16, except that the fluorine-containing diaminobenzene derivative was not used but 1.00 g (5.0 mmol) of DDE and 2.20 g (4.95 mmol) of 6FDA were dissolved in 18.1 g of N,N-dimethylacetamide.

The molecular weight of the polymer thus obtained was measured by gel permeation chromatography. As a result, the polymer had a weight average molecular weight of $1.1 \times 10^5$ in polystyrene conversion.

1.0 g of the powder was dissolved in 24 g of NMP to form a solution having a concentration of the total sold content of 4% by weight, and the solution was coated on a transparent electrode-having glass substrate by spin-coating at 3500 rpm and heat-treated at 180° C. for 60 minutes to form a uniform polyimide coat on the substrate.

Next, a cell was prepared in the same manner as in Working Example 11, using the substrate as coated above. The tilt angle of the cell was measured by a crystal rotation method to be 2.9 degrees.

COMPARATIVE EXAMPLE 4

A comparative white polyimide powder was prepared in the same manner as in Working Example 17, except that the fluorine-containing diaminobenzene derivative was not used but 2.05 g (5.0 mmol) of BAPB and 1.50 g (5.0 mmol) of TDA were used.

The molecular weight of the polymer thus obtained was measured by gel permeation chromatography. As a result, the polymer had a weight average molecular weight of $7.5 \times 10^4$ in polyethylene glycol conversion.

Next, a cell was prepared also in the same manner as in Working Example 17, and the tilt angle of the cell was measured by a crystal rotation method to be 0.6 degrees.

What is claimed is:

1. A fluorine-containing diaminobenzene derivative of a general formula (I):

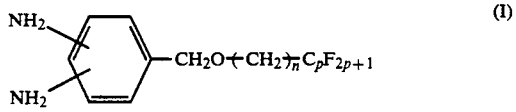

where n represents an integer of 1 to 6, p represents an integer of 1 to 12.

* * * * *